US006610834B1

(12) United States Patent
Lobo

(10) Patent No.: US 6,610,834 B1
(45) Date of Patent: Aug. 26, 2003

(54) HUMAN IGM ANTIBODIES TO CHEMOKINE RECEPTORS

(76) Inventor: Peter I. Lobo, 348 Keywest Dr., Charlottesville, VA (US) 22911

( * ) Notice: Subject to any disclaimer, the term of this patent is extended or adjusted under 35 U.S.C. 154(b) by 0 days.

(21) Appl. No.: 09/684,813

(22) Filed: Oct. 10, 2000

Related U.S. Application Data

(63) Continuation-in-part of application No. 09/439,690, filed on Nov. 15, 1999.
(60) Provisional application No. 60/108,937, filed on Nov. 18, 1998.

(51) Int. Cl.$^7$ .................... C07K 16/00; A61K 39/395; A61K 39/40; A61K 39/42
(52) U.S. Cl. ................. 530/389.6; 530/389.1; 424/136.1; 424/139.1; 424/130.1
(58) Field of Search ............ 530/387.1, 387.3, 530/387.9, 388.22, 388.23, 388.35, 388.75, 388.15, 389.1, 389.2, 389.4, 389.6, 391.1; 424/130.1, 133.1, 141.1, 142.1, 144.1, 148.1, 152.1, 154.1, 159.1, 136.1, 139.1, 160.1, 173.1; 435/5, 7.24, 69.6, 328, 331, 339.1, 343, 451, 452, 334

(56) References Cited

U.S. PATENT DOCUMENTS

| | | | | |
|---|---|---|---|---|
| 5,606,026 A | * | 2/1997 | Rodman .................. | 530/387.9 |
| 5,837,242 A | * | 11/1998 | Holliger et al. .......... | 424/136.1 |
| 5,959,085 A | * | 9/1999 | Garrone et al. .......... | 530/387.3 |
| 5,961,976 A | * | 10/1999 | Wang ............................ | 435/5 |
| 5,994,515 A | * | 11/1999 | Hoxie ...................... | 424/143.1 |
| 6,057,102 A | * | 5/2000 | Landau et al. ................. | 435/5 |
| 6,100,387 A | | 8/2000 | Herrmann et al. | |
| 6,312,689 B1 | * | 11/2001 | LaRosa .................... | 424/130.1 |

OTHER PUBLICATIONS

Garzino–Demo, et al., "B–Chemokines and Protection from HIV Type 1 Diesease," AIDS Research and Human Retroviruses, vol. 14, Supp. 2, pp. S–177–84 (1998).*
Broder, Christopher C., and Collman, Ronald G., Chemokine Receptors and HIV, Journal of Leukocyte Biology, vol. 62, pp. 20–29 (1997).*
Daniel et al, "Autoantibodies against CD4– and CD8–Positive Tlymphocytes in HIV–Infected Hemophilia patients," Vox Sang, vol. 57, pp. 172–176 (1989).*
Lacroix–Desmanzes, et al, "Self–reactive antibodies (natural autoantibodies) in healthy individuals," Journal of Immunological Methods, vol. 216, pp. 117–137 (1998).*
Liu et al, "Homozygous Defect in HIV–1 Coreceptor Accounts for Resistance of Come Multiply–Exposed Individuals to HIV–1 Infection," Cell, vol. 86, pp. 367–377 (1996).*
Fauci, et al, Harrison's Principles of Internal Medicine, 14 th Ed., McGraw Hill, Health Professions Division, N.Y. 1998.*

Hale et al., "Effects of monoclonal anti–lymphocyte antibodies in vivo in monkeys and humans", Mol. Biol. Med., vol. 1, No. 3, pp. 321–334 (1983).
Lalor et at., "Transfection of genes encoding lymphocyte differentiation antigens: applications in veterinary immunology", Vet. Immunol. and Immunopathol., vol. 17, pp. 291–302 (1987).
Jeejeebhoy et al., "Mode of recovery from the effects of heterologous anti–lymphocyte serum II. Recovery of the cells involved in antibody production", Immunology, vol. 22, pp. 801–812 (1972).
Cocchi et al., "The V3 domain of the HIV–1 gp120 envelope glycoprotein in critical for chemokine–mediated blockade of infection", Nat. Med., vol. 2, No. 11, pp. 1244–1247 (1996).
Broder et al., "Chemokine receptors and HIV", J. Leukoc. Biol., vol. 62, pp. 20–29 (1997).
Lacroix–Desmazes et al., "Self–reactive antibodies (natural autoantibodies) in healthy individuals", Journal of Immunological Methods, vol. 216 pp. 117–137 (1998).
Barbouche et al., "Spontaneous IgM autoantibody production in vitro by B Lymphocytes of normal human neonates", Scand. J. Immunol., vol. 35, pp. 659–667 (1992).
Muller et al., "Relationship of antibodies against CD4+ T cells in HIV–infected patients to markers of activation and progression: autoantibodies are closely associated with CD4 cell depletion", Immunology, vol. 79, pp. 248–254 (1993).
Stricker et al., "An AIDS–related cytotoxic autoantibody reacts with a specific antigen on stimulated CD4+ T Cells, Nature", vol. 327, pp. 710–713 (1987).
Kloster et al., "Lymphocytotoxic antibodies in the acquired immune deficiency syndrome(AIDS)", Clinical Immunology and Immunopathology, vol. 30, pp. 330–335 (1984).
Warren et al., "Specificity of anti–lymphocyte antibodies in sera from patients with AIDS–related complex (ARC) and healthy homosexuals", Clin. Exp. Immunol., vol. 73, pp. 168–173 (1988).
Sorice et al., "Anti–glycosphingolipid antibodies in HIV infection", AIDS, vol. 5, No. 3, pp. 345–346 (1991).
Morrow et al., "AIDS virus infection and autoimmunity: a perspective of the clinical, immunological, and molecular origins of the autoallergic pathologies associated with HIV disease", Clinical Immunology and Immunopathology, vol. 58, pp. 163–180 (1991).

(List continued on next page.)

Primary Examiner—James Housel
Assistant Examiner—Zachariah Lucas

(57) ABSTRACT

Human sera from normal (i.e., non-HIV infected) individuals contain certain IgM autoantibodies reactive to chemokine and other lymphocyte-surface receptors. A subset of these IgM autoantibodies that bind to such receptors, particularly CXCR4 and CCR5 receptors, can inhibit HIV-1 from infecting cells. Progression from an asymptomatic HIV-1 infected state to AIDS is determined in part by the level of IgM autoantibodies that inhibit HIV-1 from infecting cells. The claimed invention described herein is a method of using these isolated antibodies for the inhibition of the progression of virus-mediated diseases.

9 Claims, 15 Drawing Sheets

OTHER PUBLICATIONS

Dorsett et al., "Anti–lymphocyte antibodies in patients with the acquired immune deficiency syndrome", the American Journal of Medicine, vol. 78, pp. 621–626 (1985).

Daniel et al., "Autoantibodies against CD4– and CD8–positive T lymphocytes in HIV–infected hemophilia patients", Vox Sang, vol. 57, pp. 172–176 (1989).

Rodman et al., "Human immunodeficiency virus (HIV) tat–reactive antibodies present in normal HIV–negative sera and depleted in HIV–positive sera. Identification of the epitope", J. Exp. Med., vol. 175, pp. 1247–1253 (1992).

Rodman et al., "Identification of a low–affinity subset of protamine–reactive IgM antibodies present in normal, deficient in AIDS, sera: implications for HIV latency", Clinical Immunology and Immunopathology, vol. 57, pp. 430–440 (1990).

Eugen–Olsen et al., "Heterozygosity for a deletion in the CKR–5 gene leads to prolonged AIDS–free survival and slower CD4 T–cell decline in a cohort of HIV–seropositive individuals", AIDS, vol. 11, No. 3, pp. 305–310 (1997).

Navin et al., "Effect of immunoglobulin M from normal human serum on *Leishmania donovani* promastigote agglutination, complement–mediated killing, and phagocytosis by human monocytes", Infection and Immunity, vol. 57, No. 4, pp. 1343–1346 (1989).

Samson et al., "Resistance to HIV–1 infection in Caucasian individuals bearing mutant alleles of the CCR–5 chemokine receptor gene", Nature, vol. 382, pp. 722–725 (1996).

Banapour et al., "The AIDS–associated retrovirus is not sensitive to lysis or inactivation by human serum", Virology, vol. 152, pp. 268–271 (1986).

Hoshino et al., "Human T–cell leukaemia virus is not lysed by human serum", Nature, vol. 310, pp. 324–325 (1984).

Bleul et al., "The lymphocyte chemoattractant SDF–1 is a ligand for LESTR/fusin and blocks HIV–1 entry", Letters to Nature, vol. 382, pp. 829–832 (1996).

Oberlin et al., "The CXC chemokine SDF–1 is the ligand for LESTR/fusin and prevents infection by T–cell–line–adapted HIV–1", Nature, vol. 382, pp. 833–835 (1996).

Strizki et al., "A monoclonal antibody (12G5) directed against CXCR–4 inhibits infection with the dual–tropic human immunodeficiency virus type 1 isolate HIV–$1_{89.6}$ but not the T–tropic isolate HIV–$1_{HXB}$", Journal of Virology, vol. 71, No. 7, pp. 5678–5683 (1997).

Bleul et al., "The HIV coreceptors CXCR4 and CCR5 are differentially expressed and regulated on human T lymphocytes", Proc. Natl. Acad. Sci. Immunology, vol. 94, pp. 1925–1930 (1997).

Cocchi et al., "Identification of RANTES, MIP–1α, and MIP–1β as the major HIV–suppressive factors produced by CD8+ T cells", Science, vol. 270, pp. 1811–1815 (1995).

Rappaport et al., "32 bp CCR–5 gene deletion and resistance to fast progression in HIV–1 infected heterozygotes", The Lancet, vol. 349, pp. 922–923 (1997).

Trkola et al., "Genetic subtype–independent inhibition of human immunodeficiency virus type 1 replication by CC and CXC chemokines", Journal of Virology, vol. 72, No. 1, pp. 396–404 (1998).

Liu et al., "Homozygous defect in HIV–1 coreceptor accounts for resistance of some multiply–exposed individuals to HIV–1 infection", Cell, vol. 86, pp. 367–377 (1996).

Griggi et al., "Autoantibodies against ganglioside GM3 represent a portion of anti–lymphocyte antibodies in AIDS patients", Scand. J. Immunol., vol. 40, pp. 77–82 (1994).

Arenzana–Seisdedos et al., "HIV blocked by chemokine antagonist", Nature, vol. 383, p. 100 (1996).

Mouthon et al., "The self–reactive antibody repertoire of normal human serum IgM is acquired in early childhood and remains conserved throughout life", Scand. J. Immunol., vol. 44, pp. 243–251 (1996).

Marchalonis et al., "Synthetic autoantigens of immunoglobulins and T–cell receptors: their recognition in aging, infection, and autoimmunity", Proc. Soc. Exp. Biol. Med., vol. 207, pp. 129–147 (1994).

Garzino–demo et al., "β–Chemokines and protection from HIV type 1 disease", AIDS Research and Human Retroviruses, vol. 14, Supplement 2, pp. S–177–S–184 (1998).

Ugolini et al., "Inhibition of virus attachment to CD4+ target cells is a major mechanism of T cell line–adapted HIV–1 neutralization", J. Exp. Med., vol. 186, No. 8, pp. 1287–1298 (1997).

Wu et al., "Interaction of chemokine receptor CCR5 with its ligands: multiple domains for HIV–1 gp120 binding a single domain for chemokine binding", J. Exp. Med., vol. 186, No. 8, pp. 1373–1390 (1997).

Baggiolini et al., "Human chemokines: an update", Annu. Rev. Immunol., vol. 15, pp. 675–705 (1997).

* cited by examiner

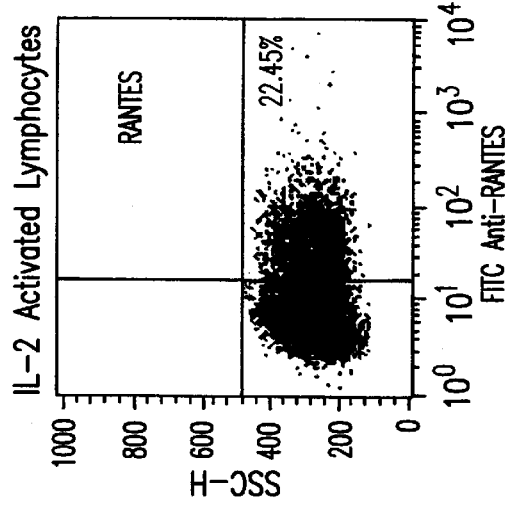
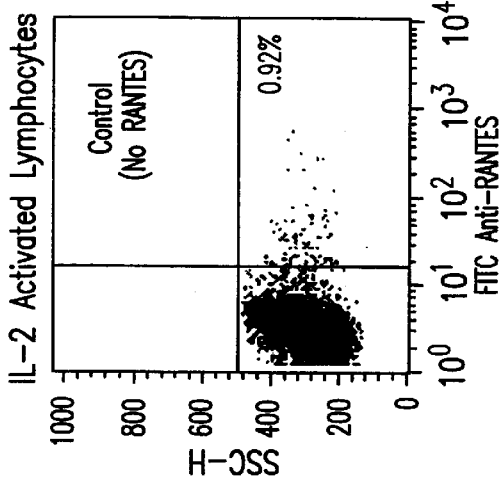
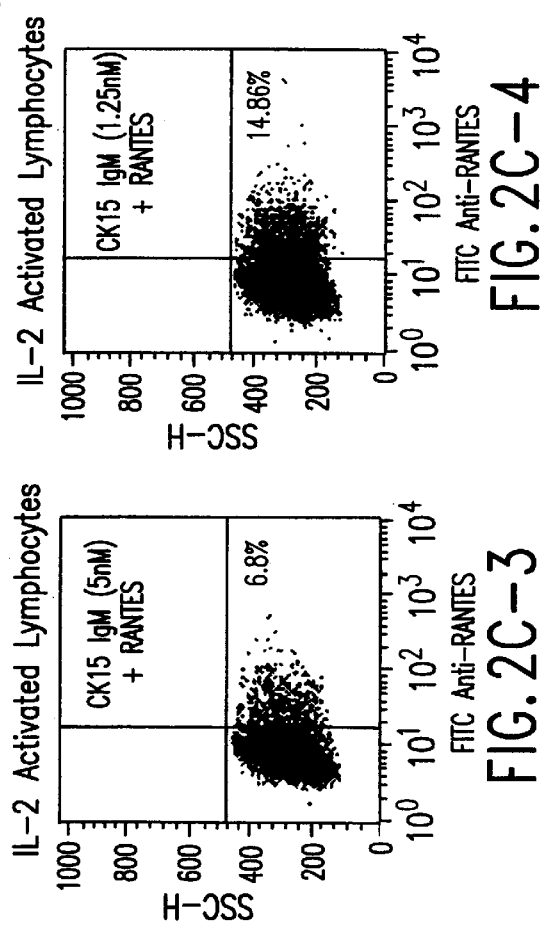

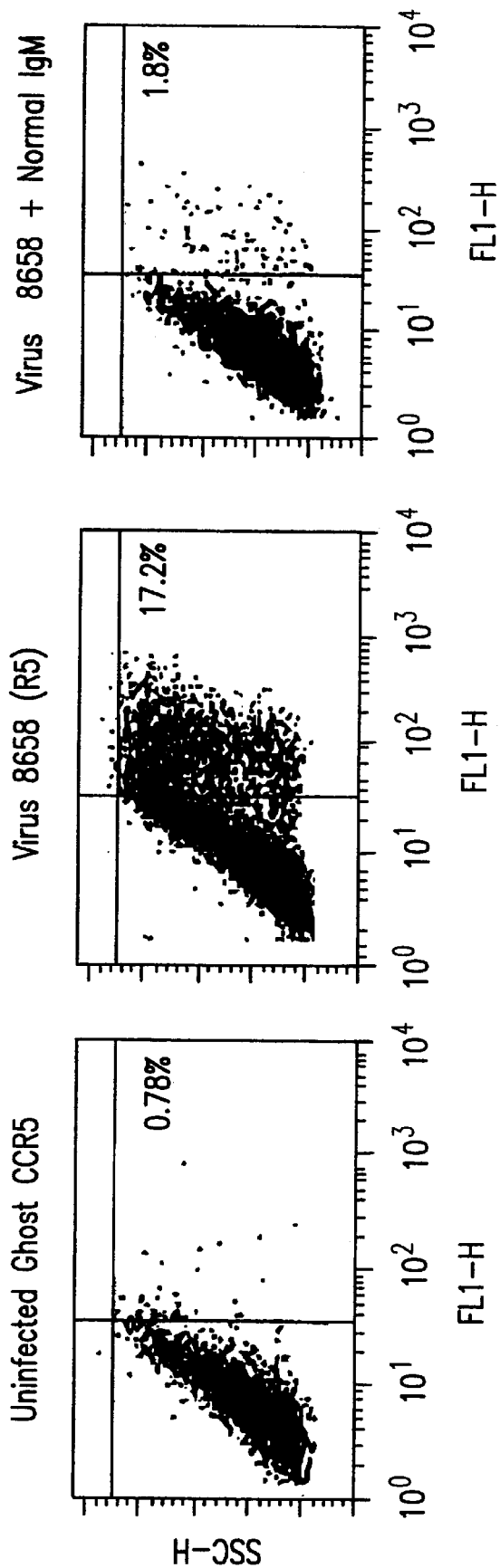

HUMAN IGM ANTIBODIES TO CHEMOKINE RECEPTORS

This application is a Continuation-In-Part of U.S. patent application Ser. No. 09/439,690, filed Nov. 5, 1999, which claims priority to U.S. Provisional Patent Application Ser. No. 60/108,937, filed Nov. 18, 1998. The entirety of those applications is incorporated herein by reference.

BACKGROUND OF THE INVENTION

1. Field of the Invention

The present invention relates generally to IgM autoantibodies and, more particularly, to a method of inhibiting disease progression.

2. Discussion of the Background

Chemokines, or chemotactic cytokines, are a class of cytokine molecules capable of chemotactically attracting migratory cells. Chemokines are essential in attracting cells to inflammatory sites irrespective of the aetiology, i.e., immunologic, infective, ischaemic, drug-induced, etc., causing the inflammation. Chemokines generally have small molecular weights in the range of about 8–10 kD.

Most chemokines can be divided into three major families, CC, CXC and CXXXC, based on the number of amino acids (referred to as "X") separating the two cysteines (referred to as "C") in the chemokine molecule. Within the CC and CXC families, chemokines are further grouped into related sub-families based on amino acid sequence similarity between them. CC chemokine sub-families include the monocyte chemoattractant protein ("MCP") sub-family and the sub-family including macrophage inhibitory protein-1α ("MIP-1α"), macrophage inhibitory protein-1β ("MIP-1β") and regulated on activation normal T cell expressed ("RANTES"). CXC chemokine sub-families include the IP-10 and Mig sub-family; the interleukin-8 ("IL-8") sub-family; and the PF4 sub-family. The chemokines stromal cell-derived factor 1α ("SDF-1β") and stromal cell-derived factor 1β ("SDF-1β") form a chemokine family that is approximately equally related by amino acid sequence similarity to the CC and CXC chemokine families. Close to 40 different chemokines have been described and cloned, each exerting a predominant functional effect. For example, RANTES attracts T lymphocytes to inflammatory sites, while IL-8 typically attracts neutrophils to inflammatory sites.

Chemokines exert their effect by binding to chemokine receptors. CC chemokines typically bind to members of the CCR class of receptors, while CXC chemokines generally bind to members of the CXCR class of receptors. These receptors are important in regulating the extent and nature of inflammation, and certain receptors tend to be localized in certain tissues and cells.

Chemokine receptors are involved in certain functions such as, for example, chemotaxis and interacting with viral proteins. The HIV-1 virus is known to bind to certain proteins on the surface of cells, i.e., the CD4 antigen on lymphocytes. However, in order to gain entrance into these cells and replicate, the HIV-1 virus must bind to another receptor, i.e., predominantly, CXCR4 and CCR5 chemokine receptors. Different HIV-1 viral strains use specific chemokine receptors, i.e., the X4 virus uses CXCR4 receptors, while the R5 virus uses CCR5 receptors.

Viral entry through chemokine receptors is of prime importance in influencing viral replication and disease progression after HIV-1 infection. For example, individuals with genetic defects in chemokine receptors have been associated with a prolonged latency period after HIV-1 infection, i.e., progression of HIV-1 to AIDS.

Researchers and pharmaceutical companies have begun looking into strategies to block or inactivate specific chemokine receptors in an effort to inhibit HIV-1 viral replication, especially because fresh human sera and their antibodies (including Immunoglobulin G ("IgG") anti-HIV-1) have no direct lytic or neutralizing activity on the HIV-1 virus. Some of these strategies include the use of peptides and IgG monoclonal antibodies that will bind to specific chemokine receptors. Such strategies, however, have not been shown to be effective.

Normal (i.e., non-infected) individuals have in their blood low levels of circulating Immunoglobulin M ("IgM") antibodies that bind to their own leukocytes such as, for example, B and T lymphocytes, without causing cell lysis at 37° C. Such IgM antibodies are, therefore, typically referred to as "anti-lymphocyte autoantibodies." These antibodies may also be referred to herein as "IgM anti-leukocyte antibodies" or "IgM anti-leukocyte autoantibodies" because they bind to macrophages and neutrophils in addition to lymphocytes and, furthermore, because they bind to allogenic leukocytes in addition to autologous leukocytes. Very little is known about the leukocyte or lymphocyte antigens or receptors that bind to IgM autoantibodies. Levels of such anti-leukocyte autoantibodies increase during inflammatory states, including autoimmune diseases and infectious diseases (i.e., virus-mediated diseases) such as, for example, systemic lupus erythematosus ("SLE"), sarcoidosis, HIV-1, malaria, Epstein-Barr virus ("EBV") and cytomegalovirus ("CMV"). Individuals with asymptomatic HIV-1, therefore, have high levels of IgM anti-leukocyte autoantibodies. The inventor's studies show, however, that chemokine receptors are one of the cell membrane receptors that bind to these IgM autoantibodies and that, through this mechanism, such IgM autoantibodies inhibit HIV-1 from infecting cells. The inventor's studies also show that IgM autoantibodies that bind to chemokine receptors are heterogeneous and that only some of these antibodies have the ability to inhibit HIV-1 from infecting cells. Levels of IgM antibodies that inhibit HIV-1 from infecting cells are very low or are undetectable in patients with AIDS. Thus, while individuals with asymptomatic HIV-1 infection have increased levels of IgM autoantibodies that inhibit HIV-1 infectivity, these levels, however, significantly decrease as the disease progress to AIDS. Total serum IgM does not decrease, however, as the disease progresses to AIDS.

The physiological and pathological functions of IgM autoantibodies that bind lymphocytes remain unknown because, in part, very little is known about which membrane receptors are recognized and are bound by these IgM autoantibodies. It is unresolved, therefore, whether the increased production of these IgM autoantibodies after a viral infection is merely a non-specific response resulting from direct polyclonal activation of B cell precursors by EBV and/or the gp120 glycoprotein or is designed for a specific purpose, i.e., to function as protective antibodies. That the normal B cell repertoire has a high frequency (about 3 to 10%) of B cells committed to the production of IgM autoantibodies supports the theory that such increased production of IgM autoantibodies is designed for a specific purpose.

SUMMARY OF THE INVENTION

Normal individuals have naturally occurring IgM autoantibodies (referred to as IgM NAA), which are present at birth. IgM NAA are mostly polyreactive and do not lyse cells at body temperature. While the presence of IgM anti-leucocyte NAA has previously been described, there is no prior art identifying the leukocyte receptors targeted by IgM, nor is there prior art showing that IgM anti-leukocyte NAA can alter cell function or inhibit viral infectivity of leukocytes In the present invention, applicant has discovered that some of these non-lytic IgM anti-leukocyte NAA obtained from normal human sera specifically inhibit binding of chemokines to their receptors, enhance or inhibit chemotaxis and inhibit HIV-1 from infecting cells. IgM autoantibodies that inhibit HIV-1 from infecting cells are depleted in patients with AIDS but not in asymptomatic HIV-1 infected individuals or in normal individuals. Moreover, IgM anti-leukocyte NAA are a heterogenous group of antibodies that bind to other non-chemokine receptors on the leukocyte.

Accordingly, one object of the present invention is to provide a method of inhibiting virus-mediated disease progression through use of IgM anti-leucocyte NAA.

The above and other objects, advantages and features of the present invention will become more apparent from the following detailed description of the presently preferred embodiments, when considered in conjunction with the figures, and to the appended claims.

BRIEF DESCRIPTION OF THE DRAWINGS

FIG. 2C is a dot plot FASCAN display depicting CK15 IgM inhibition of RANTES binding to IL-2-activated human lymphocytes.

FIGS. 5A–5C depict the effect of various IgM levels on HIV-1 R5 and X4 infectivity of Ghost cells.

DESCRIPTION OF THE PREFERRED EMBODIMENTS

Figure 1A:
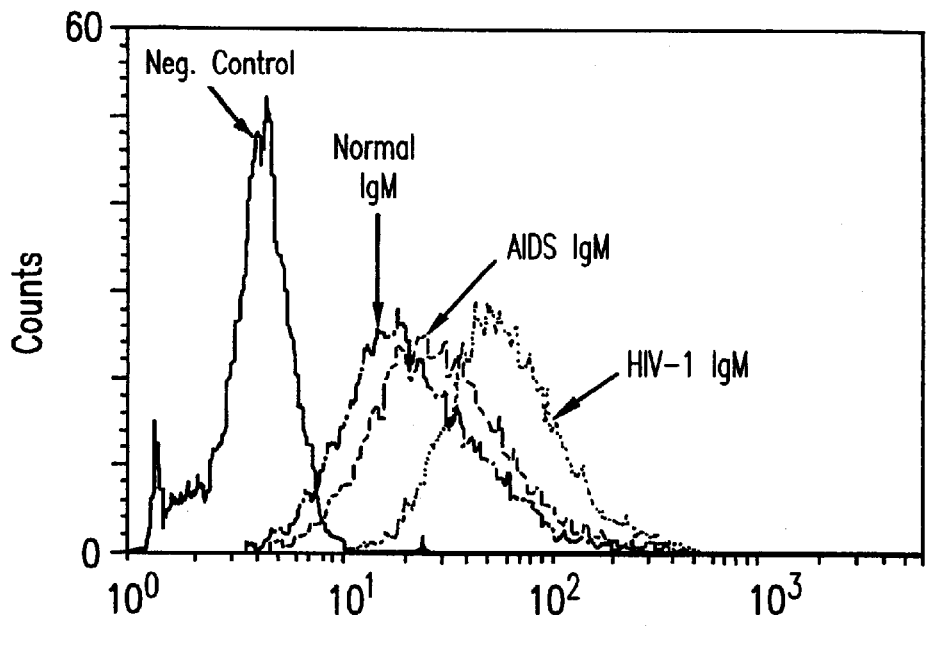
FIG. 1A is a graph depicting binding of Normal IgM, HIV IgM and AIDS IgM to Sup T-1 cells.

To achieve the foregoing and other objects, and in accordance with the purpose of the present invention as embodied and broadly described herein, the present invention relates to the expression, stimulation and administration of IgM receptor-binding antibodies to address viral infections and disease states induced thereby.

The IgM autoantibodies in the blood of normal individuals have been found to bind to various extracellular receptors present on lymphocytes. Such receptors include, but are not limited to, chemokine receptors and other lymphocyte-surface receptors. Representative chemokine receptors are, for example, CXCR4, CCR5, CCR3 and CCR2b. Representative lymphocyte-surface receptors include, for example, glycolipid receptors.

According to the present invention, IgM anti-lymphocyte autoantibodies present in normal sera bind to chemokine and other lymphocyte-surface receptors and, through this mechanism, inhibit HIV-1 from infecting cells. These IgM autoantibodies prevent lymphocytes from being infected with HIV-1.

Human sera from normal, uninfected individuals contain low levels of IgM anti-leukocyte autoantibodies reactive with chemokine and other leukocyte-surface receptors. These anti-leukocyte antibodies increase after HIV-1 infection and may play a role in the slow progression of HIV-1 disease by limiting entry of the virus into lymphocytes, macrophages and other cells. IgM anti-chemokine receptor antibodies function as "blocking" antibodies as they are not cytolytic at 37° C.

While not wishing to be bound to a specific theory, it is believed that normal individuals are born with the capacity to form IgM autoantibodies to chemokine and other lymphocyte-surface receptors. These IgM autoantibodies do not damage the cells bearing chemokine receptors because these antibodies cannot activate complement at body temperature (37° C.). It is also believed that these IgM autoantibodies are heterogeneous and function normally to regulate receptor expression and are protective (i.e., prevent viral entry into cells). A subset of IgM anti-chemokine receptor autoantibody inhibits HIV-1 from infecting cells. It is further believed that the increase in these antibodies after HIV-1 infection protects individuals from developing AIDS in less than one year. Depletion of IgM, which inhibits HIV-1 from infecting cells in AIDS patients but not in asymptomatic HIV-1 infected individuals indicates, therefore, that the presence of such IgM autoantibodies may be important in slowing down disease progression in the event of viral infection or other virus-mediated disease.

EXPERIMENTAL STUDIES

Methods/Procedures

Cell Lines

Sup T-1 and Jurkat cells are lymphoma T cell lines expressing the CXCR4 chemokine receptor. These cell lines are obtained from the AIDS Reagent Program at NIH.

An HOS osteosarcoma cell line is co-transfected with CD4 and either CXCR4 or CCR5 genes to produce HOS-CD4, HOS-CD4-CXCR4 and HOS-CD4-CCR5 cells. Ghost CCR5 and Ghost CXCR4 are HOS-CD4 cells co-transfected with the HIV-2 LTR driving hGFP construct and either CCR5 or CXCR4 genes, respectively. The cell line and the transfectants are obtained from the AIDS Reagent Program at NIH.

A glioblastoma cell line, U373-MAGI, is co-transfected with CD4 and either CXCR4 or CCR5 to produce U373-MAGI-CXCR4 and U373-MAGI-CCR5, respectively. Again, the cell line and the transfectants are obtained from the AIDS Reagent Program at NIH.

All of the transfected cell lines stably express CCR5 or CXCR4, with-the U373-MAGI cells having the highest expression of these receptors.

Human peripheral blood lymphocytes ("PBL") is activated with IL-2 to enhance CCR5 expression. PBL ($2\times10^6$ cells in 1 ml RPMI culture media containing 10% fetal calf serum are activated by initially pre-treating ficol/hypaque separated PBL with IL-2 (40 units/ml) and phytohemagglutinin ("PHA-P", 5 mcg/ml) and then washing the PBL after the cells are cultured at 37° C. in about 5% $CO_2$ for 24 to 48 hours. Such PHA pre-treated cells are then kept growing for about another 6 to 7 days supplemented with 20% fetal calf serum and IL-2 (40 units/ml) before being used in chemokine binding assays.

HIV-1 Viruses

The R5 HIV-1 virus used to infect Ghost CCR5 is obtained from Dr. Homayoon Garadegan at Johns Hopkins University. The X4 virus IIIB and RF used to infect Ghost CXCR4 is obtained from the AIDS Reagent Program at NIH.

IgM Preparations and Sera

Human IgM is obtained from the following sources: affinity purified, pooled IgM obtained from sera of normal, healthy individuals (referred to as "affinity purified Accurate IgM") available from Accurate Chemicals of Westbury, N.Y. (catalog number AI-MO2); IgM purified by size exclusion chromatography from pooled, heat-inactivated sera (56° C.) of normal, healthy individuals (referred to as "Normal IgM"), from asymptomatic patients with HIV-1 infection (referred to as "HIV IgM") and from patients diagnosed with AIDS (referred to as "AIDS IgM"); and culture supernatants of EBV transformed human B cell clones. Size exclusion chromatography (Sephacryl S-300 HR) is used to remove low molecular weight substances (i.e., chemokines, antiviral drugs, etc.) and IgG anti-HIV-1 antibodies that could affect the experiment.

The HIV IgM is pooled from seven asymptomatic HIV-1 infected patients not taking antiviral agents. The HIV-1 infected patients all have greater than 500 CD4 positive cells per ml and a DNA viral load of less than 2,000. The AIDS IgM is pooled from nine AIDS patients having an opportunistic infection and less than 150 CD4 positive cells per ml and a viral load of greater than 10,000 despite antiviral agents. Normal IgM from six normal, healthy subjects is used either individually or pooled. Data exemplified in the drawings are from pooled IgM unless otherwise indicated.

The culture supernatants of EBV transformed human B cell clones are separated by Sephacryl S-300 HR column chromatography, which separates proteins by size. The human B cell clones are derived from B lymphocytes isolated from the blood of a patient with SLE. The B cell clones are developed by infecting B cells with the EBV virus, which makes the B cells immortal and capable of secreting a specific antibody, i.e., IgM. More particularly, non-T cells are isolated from PBL after removal of T cells using a sheep erythrocyte rosetting technique. About $2\times10^3$ non-T cells in about 0.1 ml RPMI 1640 cell culture media containing about 10% fetal calf serum are added to each well of a 96-well plate. To each well is then added about 50 lambda of EBV-containing B95-8 cell line supernatant. Before incubation, about $10^4$ allogenic irradiated (3,000 rads) PBL in 0.05 ml are added as feeder cells. The plates are incubated at 37° C. in about 5% $CO_2$. The culture medium is replaced about every 4 to 5 days. After about 3 to 4 weeks, B cell lines appear as "clumps" in the wells. Feeder cells die during this period. When the "clumps" appear, these clumped cells are transferred to a 24-well plate, i.e., cells from one well are transferred into a single larger well. Culture media is changed when the media changes to a yellowish color, usually about 3 to 5 days. After about 2 weeks, supernatants are checked for IgM antibody. Wells containing lines with desired antibody specificity are further subcloned with limiting dilution in a 96-well plate. About $10^5$ feeder cells are added to each well containing these lines. Supernatants are rechecked to isolate clones with desired antibody specificity. Supernatants are refrigerated, but not frozen as IgM can precipitate out. Clones secreting IgM antibodies that are useful in inhibiting HIV-1 infectivity are cryopreserved. Supernatants from such clones usually contain about 0.5 to about 0.7 $\mu$g/ml antibody. Clones of particular interest can be fused with K6H6/B5 plasmacytoma cell line to develop hybridomas. The clones are screened to identify and obtain those clones that react with CCR5 and CXCR4 chemokine receptors present on the transfected cells. Such clones have increased IgM binding by flow cytometry to the HOS-CD4 transfectants (i.e., HOS-CD4-CXCR4 and HOS-CD4-CCR5) when compared to the HOS-CD4 control.

Any contaminating IgG is removed from the IgM preparations that is isolated from the sera and the culture supernatants by exposure to both protein G-Agarose (available from Sigma) and goat anti-human IgG (Fc specific)-Agarose (available from Sigma).

IgM is also obtained using Sephacryl S-300 HR column chromoatography from sera of a patient diagnosed with Waldenstrom macroglobulinemia (a form of B cell lymphoma) and which, on serum protein electrophoresis, has a single peak for IgM (monoclonal). This latter IgM preparation is hereinafter referred to as "Waldenstrom IgM."

Chemokines

Four chemokines preparations are used in the following studies. RANTES, SDF-1α and biotin-labeled SDF-1α are obtained from Becton Dickinson of La Jolla, Calif. Radio-labeled RANTES (referred to as "$I^{125}$ RANTES" or "$I^{125}$") is obtained from NEN Life Science of Boston, Mass. RANTES binds to CCR5, while SDF-1α binds to CXCR4.

IgG Antibodies

Two murine IgG monoclonal antibodies, 12G5 and 2D7, specific for CXCR4 and CCR5, respectively, are used. The 12G5 is obtained from Becton Dickinson, while the 2D7 is obtained from the AIDS Reagent Program.

Quantitation of IgM Binding to Cells

Flow cytometry is used to quantify IgM binding to the cells. Prior to flow cytometry, about $1\times10^5$ cells are initially incubated at about 4° C. with about 150 nM of each of Normal IgM, HIV IgM and AIDS IgM. The cells are then washed, followed by staining with fluorescein-isothiocyanate ("FITC") goat anti-human IgM (Fc specific). Binding of IgM to human peripheral blood T lymphocytes is quantified by two color flow cytometries, i.e., using phyco-erytherin ("PE")-labeled anti-CD3 and FITC-labeled goat anti-human IgM (Fc specific).

IgM Binding to Cell Membrane Proteins

Western blot assays are conducted to determine if IgM autoantibodies bind to cell membrane proteins. Four controls are made by combining about 50 $\mu$g of crude membrane proteins obtained from U373-MAGI with about 100 $\mu$l supernatant from four different EBV transformed B cell clones. Two additional controls are made by combining about 50 μg of crude membrane proteins obtained from U373-MAGI with about 100 μl each of HIV-1 serum and AIDS serum. These controls are compared to cell membrane proteins obtained from the same cell line, but transfected with and expressing either CXCR4 or CCR5, and prepared in the same manner.

IgM Inhibition of $I^{125}$ RANTES Binding to CCR5

Various studies are employed to determine if IgM inhibits binding of chemokines to chemokine receptors. In this study, the focus is whether IgM with anti-CCR5 activity can inhibit binding of $I^{125}$ RANTES to CCR5. This study is performed with affinity purified IgM and with supernatants from EBV transformed B cell clones, specifically, CK15. Controls are supernatants containing IgM Rheumatoid factor and purified human IgG.

The first approach is to determine if affinity purified Accurate IgM and/or CK15 IgM inhibit binding of $I^{125}$ RANTES to non-denatured, crude membrane proteins obtained from U373-MAGI-CCR5. Here, each of affinity purified Accurate IgM and CK15 IgM or 500 fold unlabeled RANTES relative to labeled RANTES in varying molar concentrations ranging from about $10^{-6}$ to about $10^{-10}$ are incubated with about 5 μg of non-denatured U373-MAGI-CCR5 membrane proteins for about 1 hour at room temperature in the presence of $Ca^{+2}$ and $Mg^{+2}$ and a protease inhibitor. At the end of the incubation, about 0.25 nM $I^{125}$ RANTES available from NEN Life Science is added to each mixture, and each mixture is further incubated at room temperature for about another 2 hours. Each mixture is then harvested over fiberglass filters and washed three times to remove unbound $I^{125}$ RANTES. Specific $I^{125}$ RANTES binding is calculated by subtracting the counts of radioactivity per minute ("c.p.m.") of $I^{125}$ RANTES when used with 500 fold molar excess of unlabeled RANTES from the data obtained with $I^{125}$ RANTES.

In a second approach, IgM inhibition of $I^{125}$ RANTES binding to CCR5 is detected by Western blotting. Here, about 250 μg of non-denatured U373-MAGI-CCR5 membrane proteins are incubated, under non-reducing conditions, with each of about 0.1 nM Normal IgM, 350 nM IgG, 0.4 mcM unlabeled RANTES and a culture media control at room temperature for about 1 hour prior to adding about 1.0 nM $I^{125}$ RANTES available from NEN Life Science to each mixture. After about 2 hours incubation, about 5 nM of a cross-linker (BS-3 available from Pierce of Rockford, Ill.) is added to each mixture to crosslink amine residues on $I^{125}$ RANTES bound to CCR5. Also, $I^{125}$ RANTES in the absence of U373-MAGI-CCR5 membrane proteins is used. Each mixture is then electrophoresed onto 12% gel SDS-PAGE, and radiographs of the gel are obtained.

IgM Inhibition of RANTES Binding to CCR5 on Intact Cells

A procedure is used to determine if IgM inhibits binding of RANTES to CCR5 receptors present on intact cells, e.g., U373-MAGI-CCR5E and IL-2-activated human lymphocytes. About $1 \times 10^5$ cells are initially incubated at room temperature for about 45 minutes with RPMI media containing about 10% fetal calf serum or with about 150 nM of affinity purified Accurate IgM or with about 400 nM purified human IgG or with about 5 nM, about 125 nM or about 0.45 nM of CK15 IgM prior to adding about 1 microgram of RANTES to each mixture. The cells are then re-incubated for about 90 minutes at 4° C. and then washed at 4° C. Goat anti-RANTES antibody (obtained from R&D of Minneapolis, Minn.) is then added, and the cells are incubated for about 45 minutes at 4° C. prior to being washed and then stained with FITC rabbit anti-goat antibody. The quantity of FITC-labeled RANTES binding to CCR5 on these cells is analyzed by flow cytometry.

IgM Inhibition of SDF-1α Binding to CXCR4 on Intact Cells

A procedure is used to determine if IgM inhibits binding of SDF-1α to chemokine receptors (i.e., CXCR4) present on intact Sup T-1 cells. About $1 \times 10^5$ Sup T-1 cells are initially incubated at room temperature for about 45 minutes with RPM 1 media containing about 10% fetal calf serum or with about 150 nM of each of Normal IgM, HIV IgM and AIDS IgM or with about 5 nM of each of Waldenstrom IgM and CK15 IgM prior to adding about 25 ng of biotin-labeled SDF-1α to each mixture. The cells are then re-incubated for about 90 minutes at 4° C. Following re-incubation, FITC avidin is added to the cells, and the cells are washed. The quantity of FITC-labeled SDF-1α binding to CXCR4 is analyzed by flow cytometry.

IgM Inhibition of Radio-labeled IL-2 Binding to Human Lymphocytes

Additional procedures are performed to determine if IgM inhibition of chemokines binding to CCR5 or CXCR4 is indeed specific for chemokines. More particularly, these procedures are used to determine if IgM, through some non-specific mechanism, also inhibits binding of radio-labeled IL-2 to the IL-2R present on phytohemagglutinin-activated PBL using methods as previously described in, for example, Teshigawara, K. et al., J. Exp. Med., 165:223–238 (1987), which is incorporated herein by reference. Specifically, three day phytohemagglutinin-activated PBL $(1 \times 10^6)$ is incubated with $I^{125}$ labeled IL-2 (available from NEN Life Science), and the $I^{125}$ labeled IL-2 bound to PBL is quantified by overlaying the PBL over oil and centrifuging the microfuge tube to separate unbound $I^{125}$ labeled IL-2 from the cell pellet. Radioactivity of $I^{125}$ is quantitated in the cell pellet. In these procedures, PBL is interacted with each of excess unlabeled IL-2 (2.0 mcM), pooled human IgG (300 nM), IgM Rheumatoid factor and affinity purified Accurate IgM (100 nM) prior to adding $I^{125}$ labeled IL-2.

Chemotaxis Assay

A chemotaxis assay is performed with each of Normal IgM, HIV IgM, AIDS IgM and Waldenstrom IgM at concentrations of about 20 nM, about 40 nM, about 100 nM and about 200 nM IgM using 24-well Costar transwell tissue culture inserts with 5 micron polycarbonate filters. For each assay, the IgM is placed in the upper transwell containing about $2 \times 10^4$ Jurkat cells in about 0.1 ml RPM1 containing about 5% fetal calf serum. About 30 minutes later, approximately 50 ng of SDF-1α is added to the bottom well containing about 0.6 ml of the same media as in the upper well. After about 4 hours, cells migrating to the bottom well are enumerated by flow cytometry. The chemotaxic index ("CI") is calculated by dividing the total number of cells migrating in the presence of SDF-1α by the number of cells migrating in the absence of SDF-1α. The baseline chemotactic index of SDF-1α alone (i.e., without IgM) is about 3.1.

Measurement of Intracytosolic $Ca^{+2}$ Flux

Assays are performed to determine intracytosolic $Ca^{+2}$ flux using known methods, for example, as described in Haverstick, G., MD, Molecular Biol. of Cell. 4:173–184 (1993), which is incorporated herein by reference. In one assay, about 45 nM of HIV IgM is added to Jurkat cells at a time of about 20 seconds. Approximately 60 seconds later, about 100 ng of SDF-1α is added, and the magnitude of change in cytosolic $Ca^{+2}$ after adding SDF-1α is measured. A second assay is done using about 45 nM of AIDS IgM in place of HIV IgM. In a third assay, no IgM is added, but SDF-1α is still added at a time of about 80 seconds.

Temperature Dependence for the Cytolytic Effects of IgM Anti-leukocyte Antibody

Temperature dependence for the cytolytic effects of IgM anti-leukocyte antibody is evaluated by a complement dependent microlymphocytotoxicity assay. Various dilutions of IgM antibody are reacted for 1 hour with either $2 \times 10^5$ PBL or IL-2-activated PBL (7 days) before adding fresh rabbit serum as a source of complement. After about 2 hours, the cells are washed twice before adding trypan blue and enumerating dead cells that stain blue. Experiments are performed at 15° C. and 37° C.

IgM Inhibition of HIV-1 Infection of Cells

It has been observed that the HIV-1 R5 virus utilizes CCR5 receptors for cell entry, while the HIV-1 X4 virus uses CXCR4 receptors. Studies are conducted, therefore, to determine whether IgM inhibits HIV-1 infectivity in light of such observations.

In these studies, Ghost CCR5 and Ghost CXCR4 transfectant cell lines are infected with HIV-1. The Ghost cells are derived from HOS cells transfected with either CCR5 or CXCR4 genes and also co-transfected with the HIV-2 LTR driving hGFP construct. The hGFP construct enables cells infected with HIV-1 virus to emit a green fluorescence so that the number of infected cells can be quantified using flow cytometry. These cell lines are particularly suited for these studies because single-cycle viral replication can be detected in less than 48 hours.

About $2 \times 10^4$ each of Ghost CCR5 and CXCR4 cells are separately cultured for about 12 hours in about 1 ml RPM1 media containing about 10% fetal calf serum in a 12-well plate. Normal IgM is then added to each of the Ghost CCR5 and CXCR4 cells about 30 minutes prior to adding the R5 HIV-1 virus to Ghost CCR5 and the X4 HIV-1 virus to Ghost CXCR4. Both virus and antibody are present throughout the 48-hour culture period. No polybrene is used to enhance viral entry into the cells. The same procedure is repeated twice, replacing Normal IgM first with HIV IgM and then AIDS IgM.

After the 48-hour incubation period, cells are harvested and fixed in formalin. Infected cells emitting green fluorescence are enumerated with flow cytometry.

Additionally, similar data is obtained when the virus or IgM antibody is washed about 4 hours after incubating with Ghost cells.

Results

The results of the various experimental studies indicate that IgM autoantibodies bind to chemokine receptors present on lymphocytes and other cells. The results also indicate that binding of IgM autoantibodies is specific for chemokine receptors.

Binding of IgM to Cells and Cell Membrane Proteins

Figure 1B:
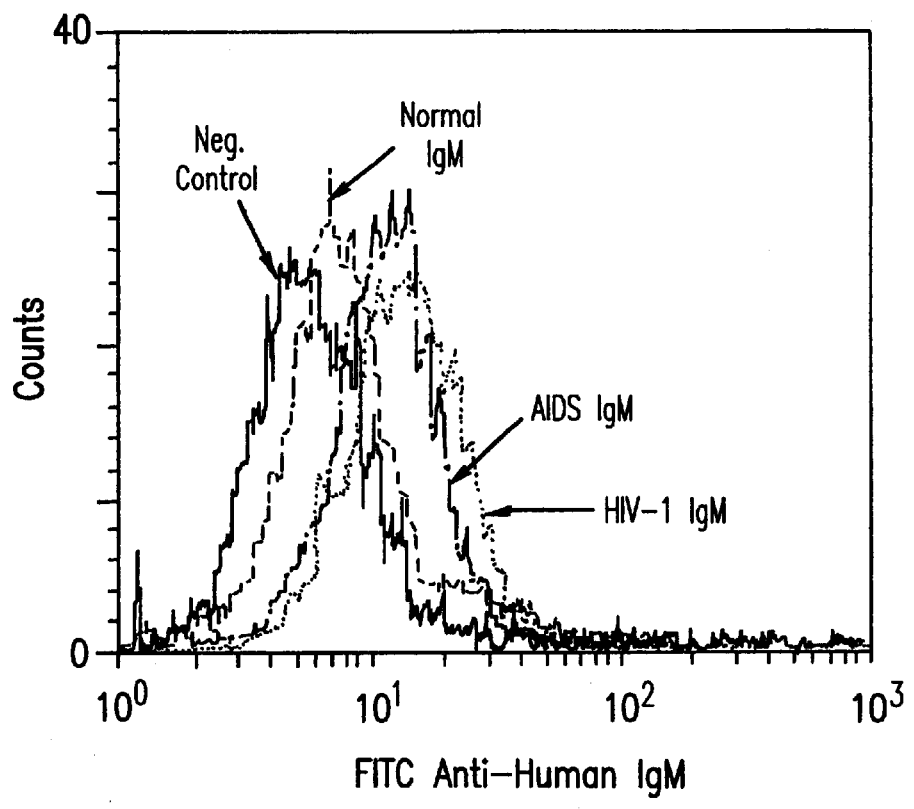
FIG. 1B is a graph depicting binding of Normal IgM, HIV IgM and AIDS IgM to Ghost CXCR4 cells.
Figure 1C:
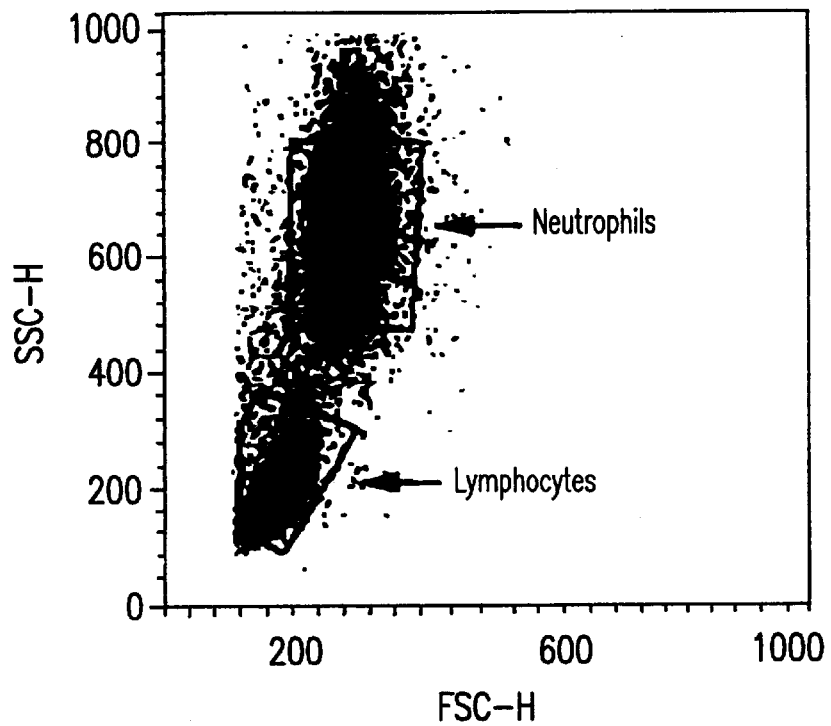
FIG. 1C is a flow cytometry (FASCAN) dot plot showing lymphocytes and neutrophils separated by size and derived from human blood.
Figure 1D:
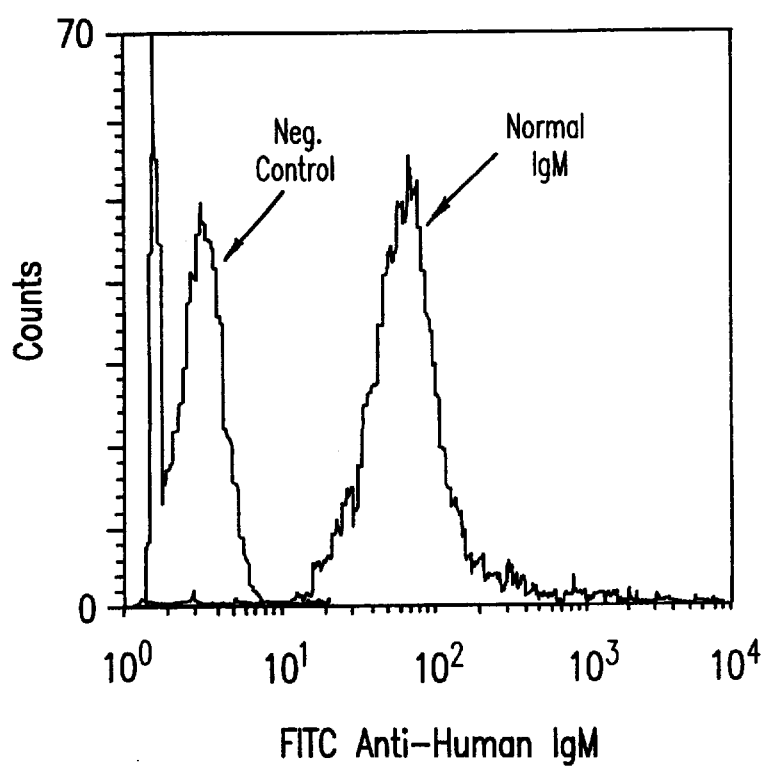
FIG. 1D is a graph depicting binding of Normal IgM to human T lymphocyte derived from peripheral blood cells.
Figure 1E:
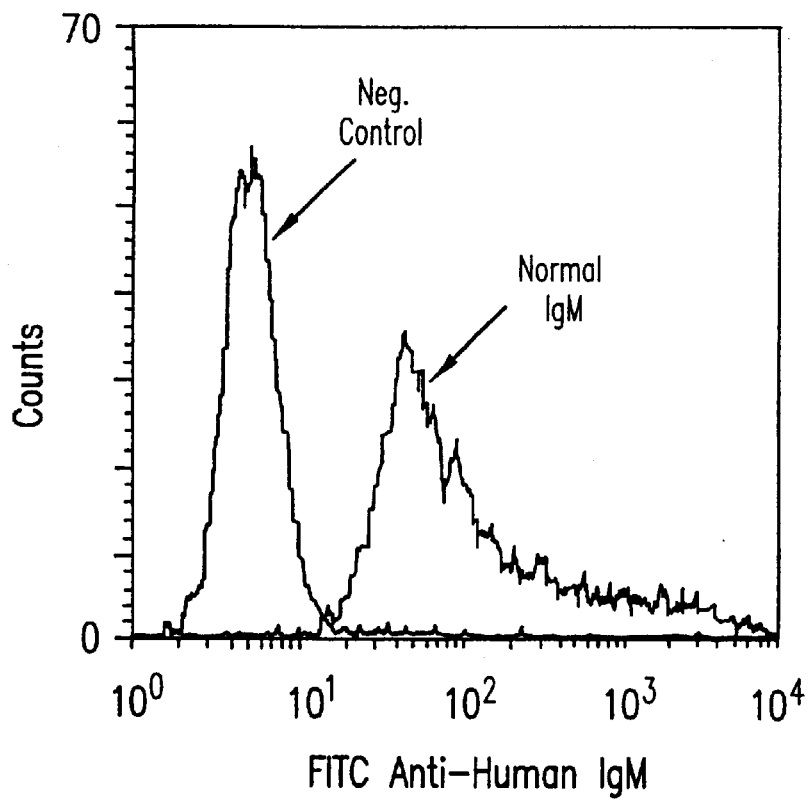
FIG. 1E is a graph depicting binding of Normal IgM to human neutrophils derived from peripheral blood cells.

The data from the above-discussed studies shows that IgM autoantibodies bind to receptors present on normal lymphocytes and malignant cells. As seen in FIGS. 1A and 1B, Normal IgM, AIDS IgM and HIV IgM contain IgM antibodies that bind to Sup T-1 (FIG. 1A) and Ghost CD4-CXCR4 cells (FIG. 1B). As seen in FIGS. 1D and 1E, Normal IgM contains antibodies that bind to T-lymphocytes isolated from peripheral blood (FIG. 1D) and neutrophils isolated from peripheral blood (FIG. 1E). The negative control in each figure indicates that no IgM was incubated with the various cells.

Figure 1F:
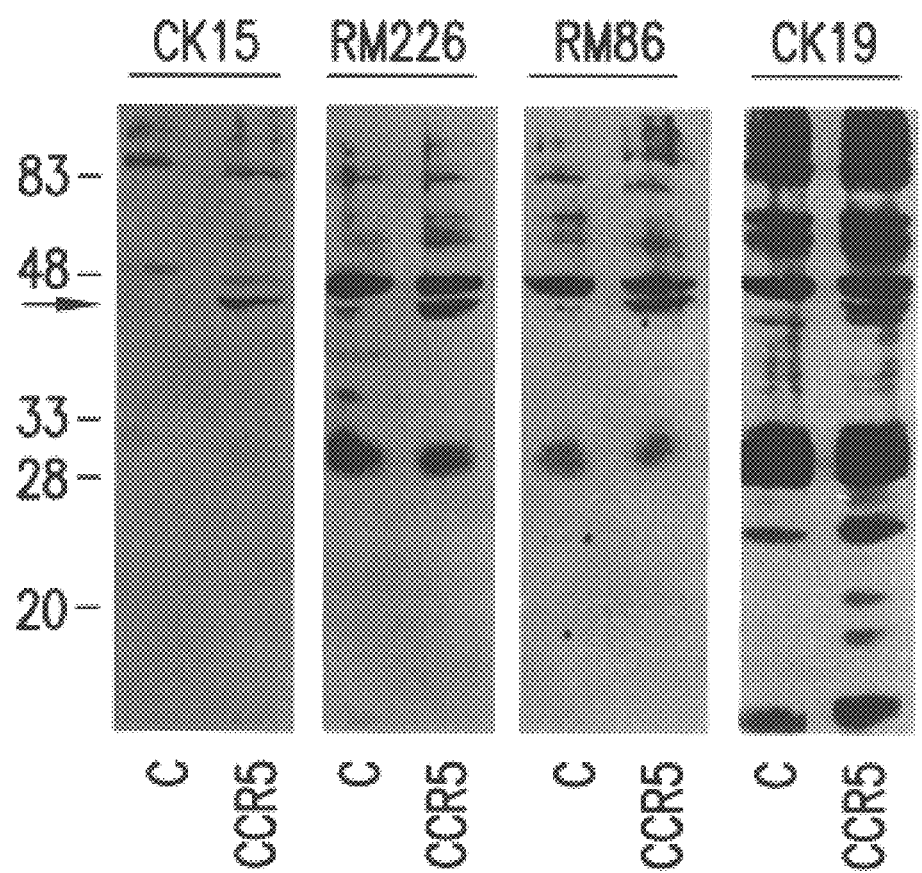
FIGS. 1F–1G are Western blot assays depicting IgM binding to cell membrane proteins obtained from U373-MAGI cells and the same cells transfected with and expressing either CXCR4 or CCR5.
Figure 1G:
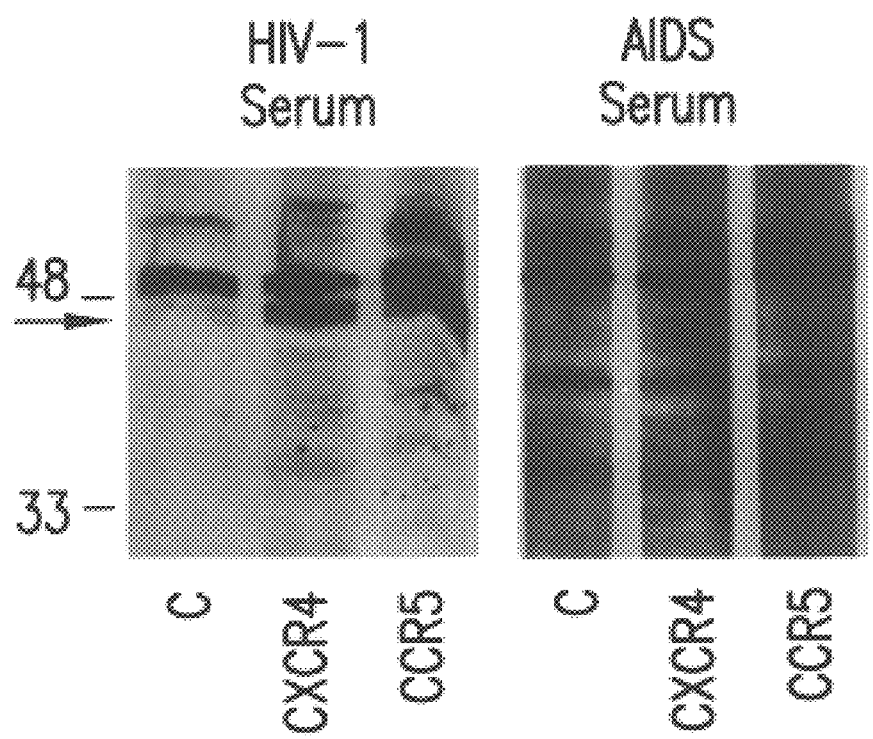

Referring now to FIGS. 1F and 1G, it is evident that IgM autoantibodies bind to several cell membrane proteins. However, IgM bound to an additional 48 kD protein present in cell lines transfected with cDNA of CCR5 ("CCR5") and CXCR4 ("CXCR4"). Membrane proteins of 48 kD are similar to the molecular weight of CXCR4 and CCR5 receptors implying, therefore, that IgM also bound to the chemokine receptors that were present in the transfected cells. IgM can bind to several membrane proteins because the IgM antibody is known to be polyreactive, especially in Western blot assays. Hence, other assay systems are employed to better define specificity of IgM binding to chemokine receptors using assays that evaluate whether IgM in a specific manner inhibits binding of chemokines to their receptor and alters chemokine receptor function.

IgM Inhibition of Chemokine Binding to Receptors

IgM autoantibodies inhibit binding of radio-labeled RANTES to CCR5 receptors but not binding of radio-labeled IL-2 to IL-2 receptors (i.e., IL-2R). This supports the concept that IgM-mediated inhibition is indeed specific for chemokines. Moreover, normal IgG does not inhibit radio-labeled RANTES from binding to CCR5 receptors.

Figure 2A:
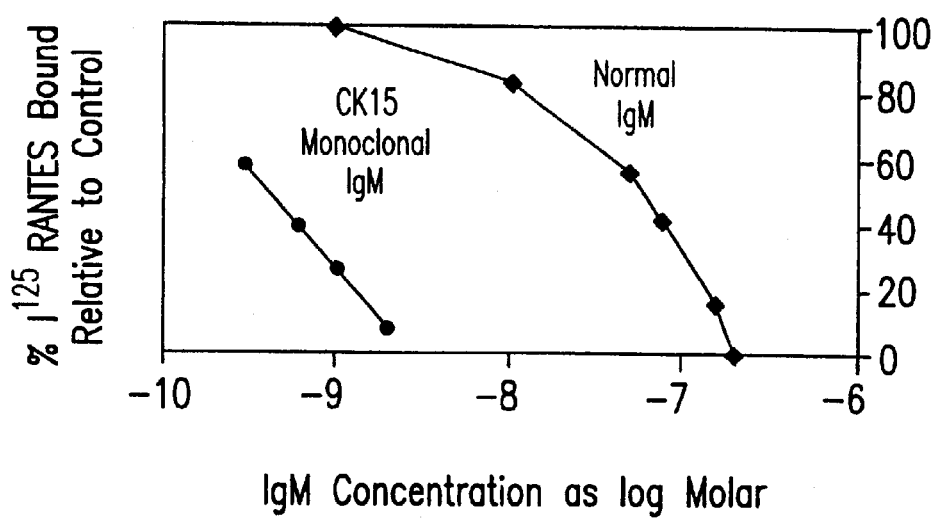
FIG. 2A is a graph depicting affinity purified Accurate IgM inhibition of $I^{125}$ RANTES binding to CCR5 present in denatured U373-MAGI-CCR5E membrane proteins as quantified by liquid scintillation.

Representative data from initial studies conducted to determine if affinity purified Accurate IgM and/or CK15 IgM inhibit binding of $I^{125}$ RANTES to non-denatured, crude membrane proteins obtained from U373-MAGI-CCR5E is depicted in FIG. 2A. As seen therein, both the affinity purified Accurate IgM and the CK15 IgM inhibit binding of $I^{125}$ RANTES to CCR5 in a dose-dependent manner. Pooled Normal IgG and IgM Rheumatoid factor, even when used at $10^6$ M, fail to inhibit binding of $I^{125}$ RANTES to CCR5. Unlabeled RANTES inhibits $I^{125}$ RANTES binding in a dose-dependent manner with a kD of 0.095 nM.

Figure 2B:
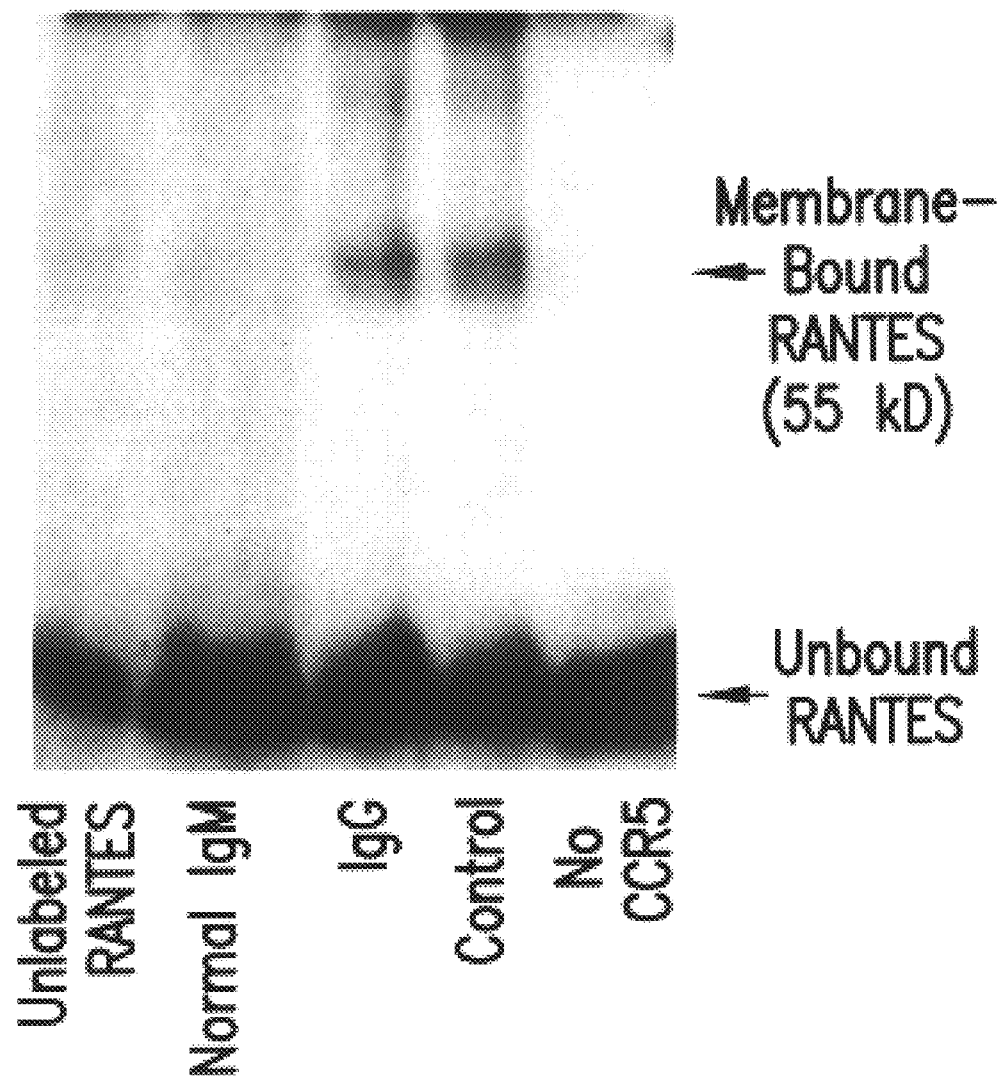
FIG. 2B is a Western blot assay depicting affinity purified Accurate IgM inhibition of $I_{125}$ RANTES binding to CCR5 present in denatured U373-MAGI-CCR5E membrane proteins.

IgM inhibition of the binding of $I^{125}$ RANTES to CCR5 as detected by Western blotting is depicted in FIG. 2B. As seen therein, affinity purified Accurate IgM and unlabeled RANTES inhibit binding of $I^{125}$ RANTES to CCR5. Neither the pooled human IgG nor the RANTES protein control inhibits binding of $I^{125}$ RANTES to CCR5. This latter observation would appear to indicate that IgM inhibition of $I^{125}$ RANTES binding to CCR5 is a result of receptor blockade and is specific for IgM having a specificity for CCR5.

Figure 2D:
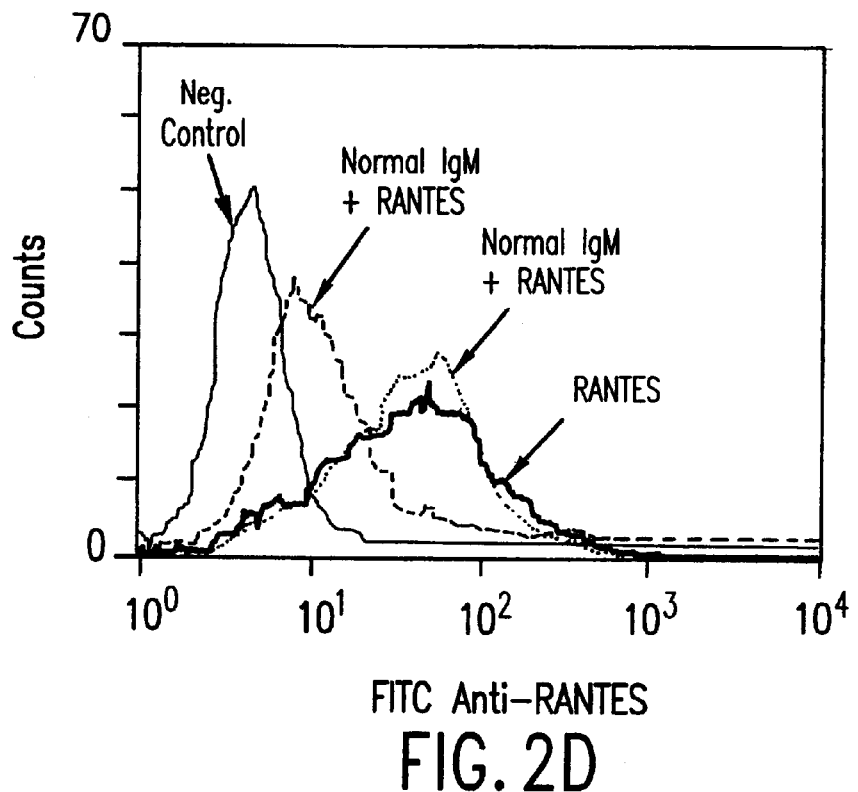
FIG. 2D is a graph depicting affinity purified Accurate IgM inhibition of RANTES binding to intact U373-MAGI-CCR5E cells.

Additional studies were performed using IL-2-activated lymphocytes, which express more CCR5 receptors when compared to unactivated lymphocytes, to determine if IgM inhibits chemokines from binding to their receptors present on intact cells. As indicated in FIG. 2C, about 22.45% of IL-2-activated lymphocytes bound to RANTES. In the presence of about 5 nM CK15 IgM, the binding decreased, with about 6.8% of the lymphocytes binding to RANTES. Less inhibition is observed with less CK15 IgM. As indicated in FIG. 2D, affinity purified Accurate IgM, but not human IgG, inhibited binding of RANTES to intact U373-MAGI-CCR5E cells.

Figure 3A:
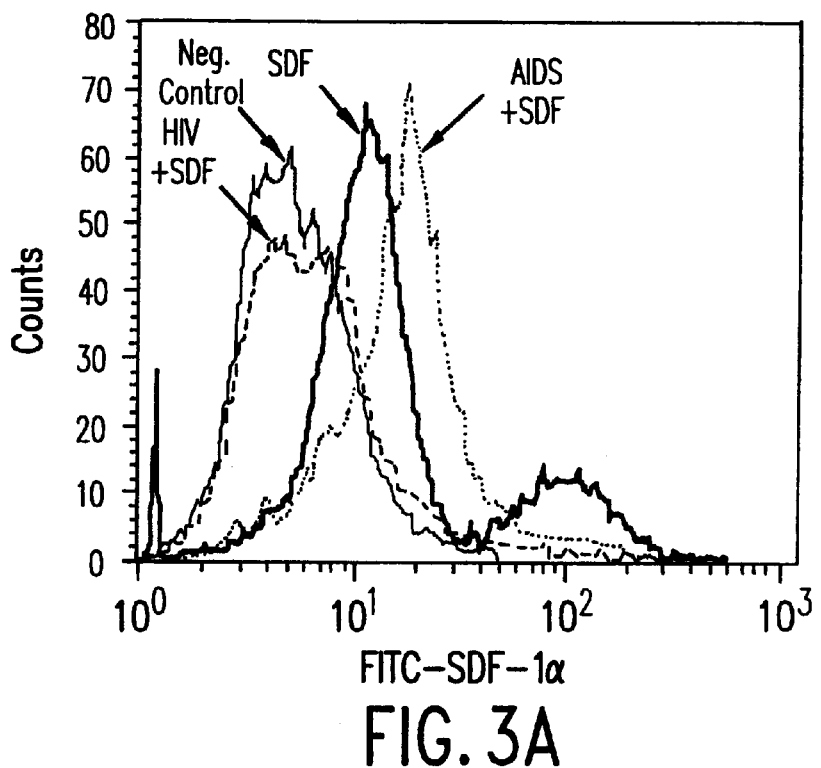
FIG. 3A is a graph depicting IgM inhibition of SDF-1α binding to CXCR4 on intact Sup T-1 cells.
Figure 3B:
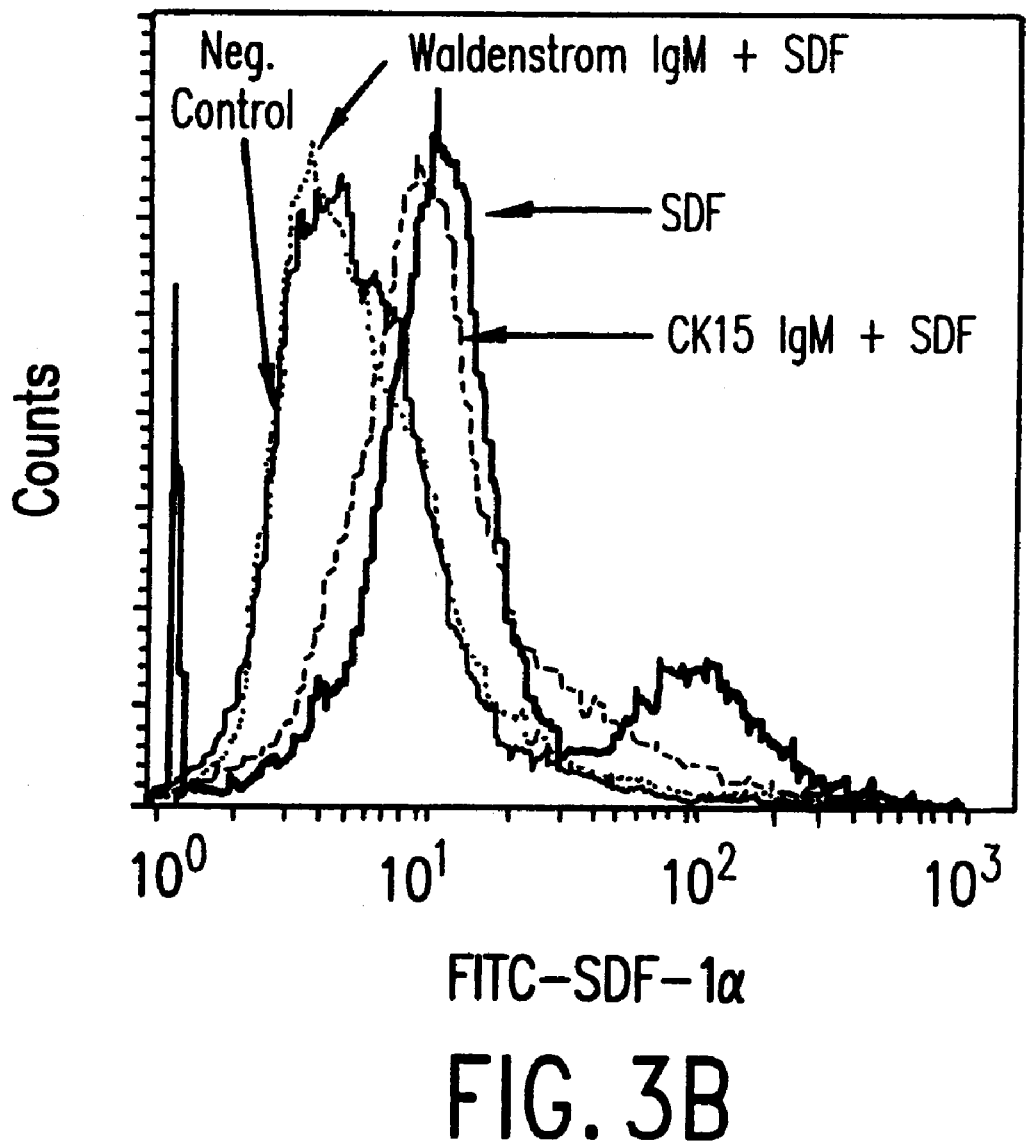
FIG. 3B is another graph depicting IgM inhibition of SDF-1α binding to CXCR4 on intact Sup T-1 cells.

As seen in FIG. 3A, Normal IgM and HIV IgM suppresses biotin SDF-1α binding, while AIDS IgM does not. A negative control is used to indicate background fluorescence of cells without IgM and SDF-1α. "SDF" indicates SDF-1α binding in the absence of IgM. Note that a small subset (15%) of Sup T-1 cells had much stronger binding to biotin SDF-1α. As seen in FIG. 3B, Waldenstrom IgM, but not CK15 IgM, inhibited binding of SDF-1α to Sup-T cells.

An additional study to determine if IgM inhibition of chemokines binding to their receptors is indeed specific for chemokines shows that binding of $I^{125}$-labeled IL-2 is inhibited by unlabeled IL-2 (>90%) and anti-TAC (anti-IL2R murine IgG antibody) but not by pooled human, affinity purified Accurate IgM, even when used at 100 nM. The results are shown in Table 1 below.

TABLE 1

INHIBITION OF I$^{125}$-LABELED IL-2 BINDING TO IL-2R ON ACTIVATED PBL

| | Specific I$^{125}$ IL-2 bound to PBMC (cpm) |
|---|---|
| Control Media | 9,468 |
| Human IgG | 8,293 |
| Human IgM | 8,809 |
| Murine anti-TAC | 1,948 |
| Unlabeled IL-2 | 2,353 |

The above results, therefore, indicate that inhibition of SDF-1α binding to CXCR4 by Normal IgM and HIV-1 IgM is specific. Data demonstrating inhibition of biotin SDF-1α binding when using Normal IgM and HIV IgM cannot be explained on basis of stearic hindrance as AIDS IgM has similar binding to Sup T-1 cells, yet fails to inhibit SDF-1α binding (see FIG. 1A). Similarly, data from FIG. 2 and FIG. 3B clearly indicate that inhibition of chemokines to their receptors by monoclonal IgM is indeed specific as Waldenstrom IgM totally inhibited binding of SDF-1α to CXCR4. The CK15 IgM, which inhibited binding of RANTES to CCR5, failed to inhibit binding of SDF-1α to CXCR4. While not wishing to be bound to any particular theory, one possible explanation is that IgM anti-leukocyte autoantibodies are heterogeneous and recognize different epitopes on the chemokine receptor. It is, therefore, possible that AIDS IgM lacks the subset of IgM antibodies that inhibit SDF-1α binding, even though the AIDS IgM binds to the chemokine receptor as will be evident from the data obtained in the chemotaxis assay (described in detail below).

Effect of IgM on Chemotaxis and Intracytosolic Ca$^{+2}$

Figures 1, 4A:
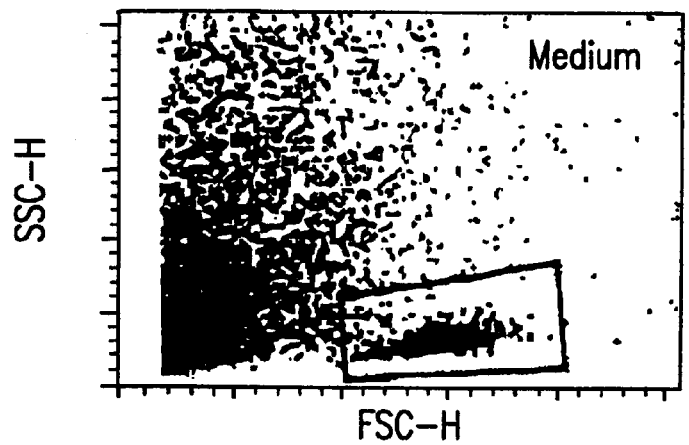
FIGS. 4A–4C indicate the effect of IgM on chemotaxis and intracytosolic $Ca^{+2}$.
Figures 2, 4A:
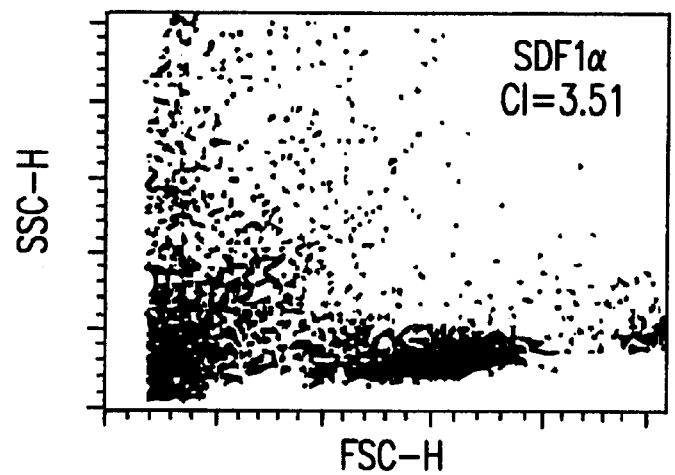
Figures 3, 4A:
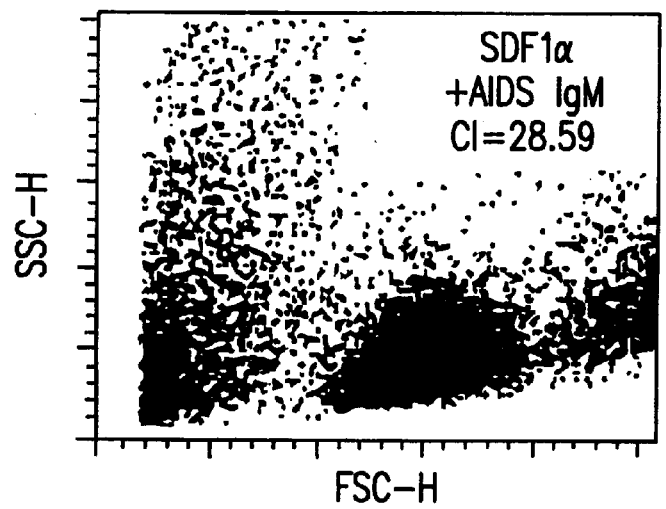
Figure 4B:
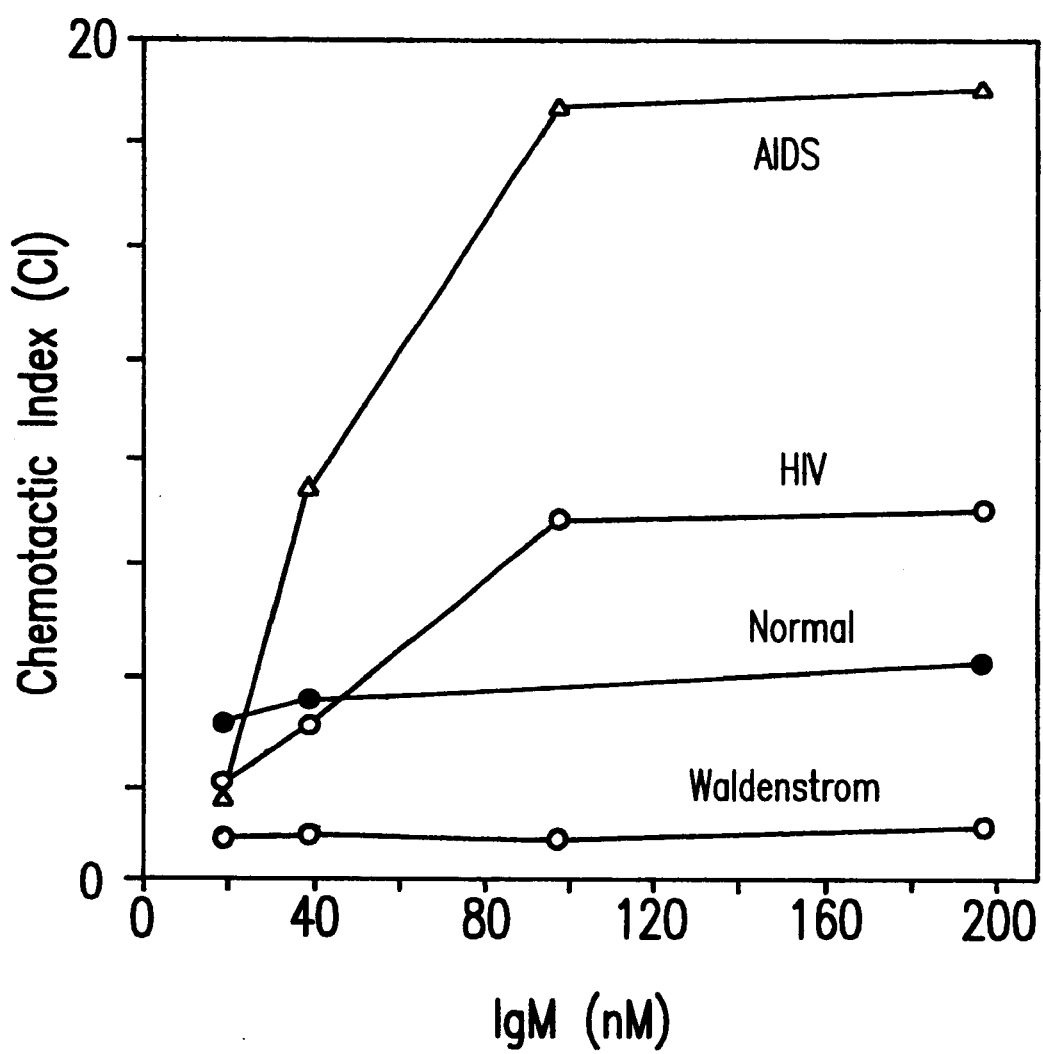
Figure 4C:
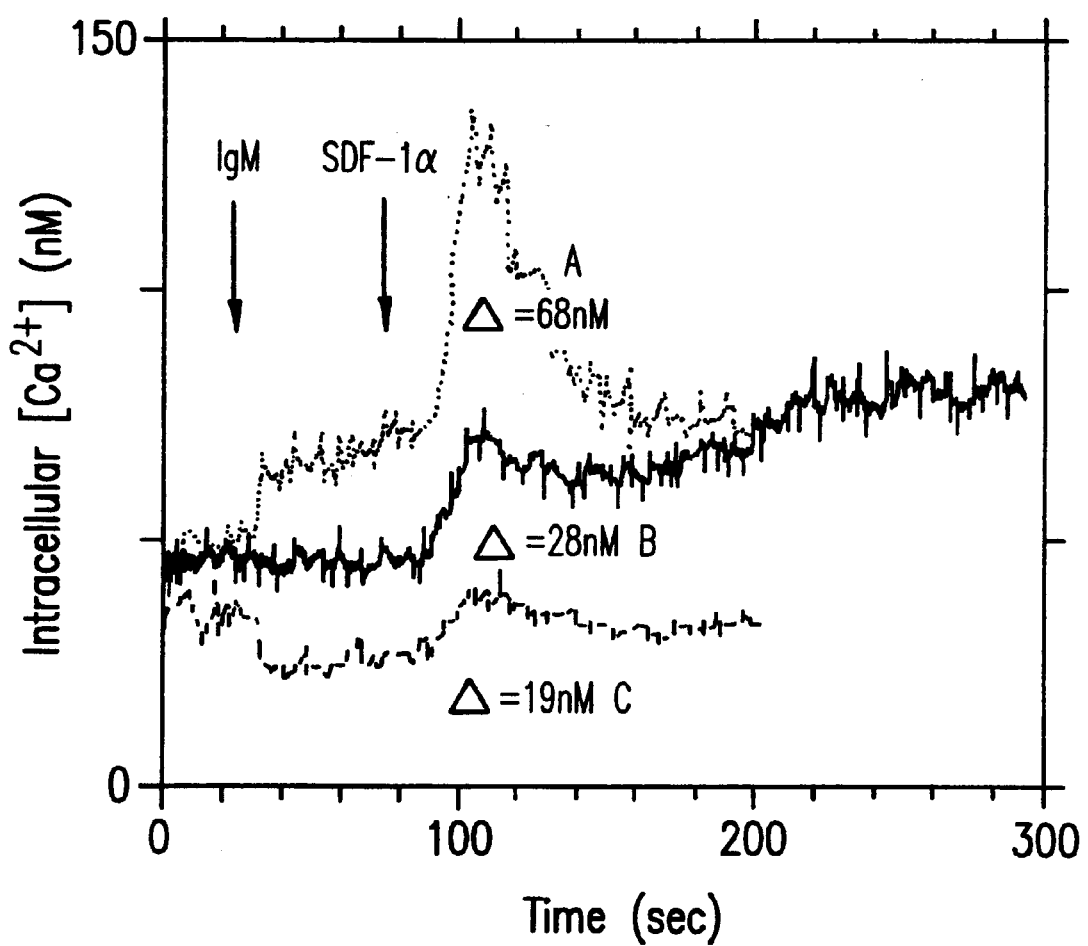

The possibility of heterogeneity of IgM is analyzed in functional assays of SDF-1α induced chemotaxis (FIGS. 4A and 4B) and intracellular Ca$^{+2}$ flux (FIG. 4C).

FIG. 4A shows flow cytometry data from another experiment to visually demonstrate the cells that have, through chemotaxis, migrated to the bottom well. Cells to be enumerated are gated to prevent enumeration of debris. All IgM preparations in the absence of SDF-1α did not affect baseline chemotaxis. In the presence of SDF-1α, however, pre-treatment of Jurkat cells with the various IgM preparations affected chemotaxis. Particularly, as seen in FIG. 4B, all pooled IgM preparations enhanced chemotaxis, with AIDS IgM showing the most enhancement. Enhanced migration into the bottom well after adding IgM to the upper well was mediated by chemotaxis-induced migration and not from some non-specific process, as adding 500 ng of SDF-1α to the upper transwell totally inhibited this enhanced migration. Control CI in the presence of SDF-1α is about 2.8. Waldenstrom IgM inhibited chemotaxis (CI=about 1.1). CK12 IgM and CK15 IgM mildly enhanced chemotaxis with the CI varying from about 5.3 to about 7.1, which is significantly more than that observed with SDF-1α alone (CI=3.1).

These findings prompted a determination of whether IgM similarly affected changes in cytosolic Ca$^{+2}$ that occur when chemokines bind to the CXCR4 receptor present on Jurkat cells. Representative data from three such experiments is depicted in FIG. 4C, where the symbol Δ indicates the magnitude of change in cytosolic Ca$^{+2}$ after adding SDF-1α. Tracing A represents Jurkat cells with AIDS IgM; tracing C represents Jurkat cells with HIV IgM; and tracing B represents Jurkat cells with no IgM. As seen in FIG. 4C, none of the IgM antibodies in the absence of SDF-1α (i.e., prior to adding of SDF-1α) elicit a rise in intracellular Ca$^{+2}$. Tracing A indicates that AIDS IgM enhances the rise in the intracellular Ca$^{+2}$ response to SDF-1α. Tracing C indicates that no enhancement occurs with HIV IgM.

Specificity of IgM interaction with CXCR4 in these Ca$^{+2}$ flux assays is ascertained by performing similar studies on another receptor present on Jurkat cells, i.e., the CD3 receptor. No enhancement in cytosolic Ca$^{+2}$ is observed by adding AIDS IgM prior to stimulating CD3 with OKT3, a murine IgG anti-CD3 antibody. Such data provides more evidence to support specificity of IgM binding to the CXCR4 receptor. Furthermore, these findings clearly support the concept of functional heterogeneity within IgM anti-lymphocyte autoantibodies, with AIDS IgM containing IgM that predominantly enhances chemotaxis and Ca$^{+2}$ flux after binding to the chemokine receptor.

Non-lytic Nature of IgM Anti-lymphocyte Antibodies at 37° C.

About 40 to 60% cell lysis was observed when the assay was performed at 15° C. Higher levels of cell lysis was observed with IL-2-activated lymphocytes, which have increased expression of chemokine receptors. Affinity purified Accurate IgM, when used at amounts of about 1.0 microgram or more, caused cell lysis, while CK15 lysed cells at concentrations of about 5 micrograms or more. When the assay was performed at 37° C., however, less than about 10% lysis was observed, and the level of lysis was similar to control cells incubated within the body. These observations are in agreement with several reports clearly demonstrating that IgM anti-lymphocyte autoantibodies are lytic at colder temperatures but not at 37° C.

Effect of IgM on HIV-1 Infection of Cells

Figure 5A:
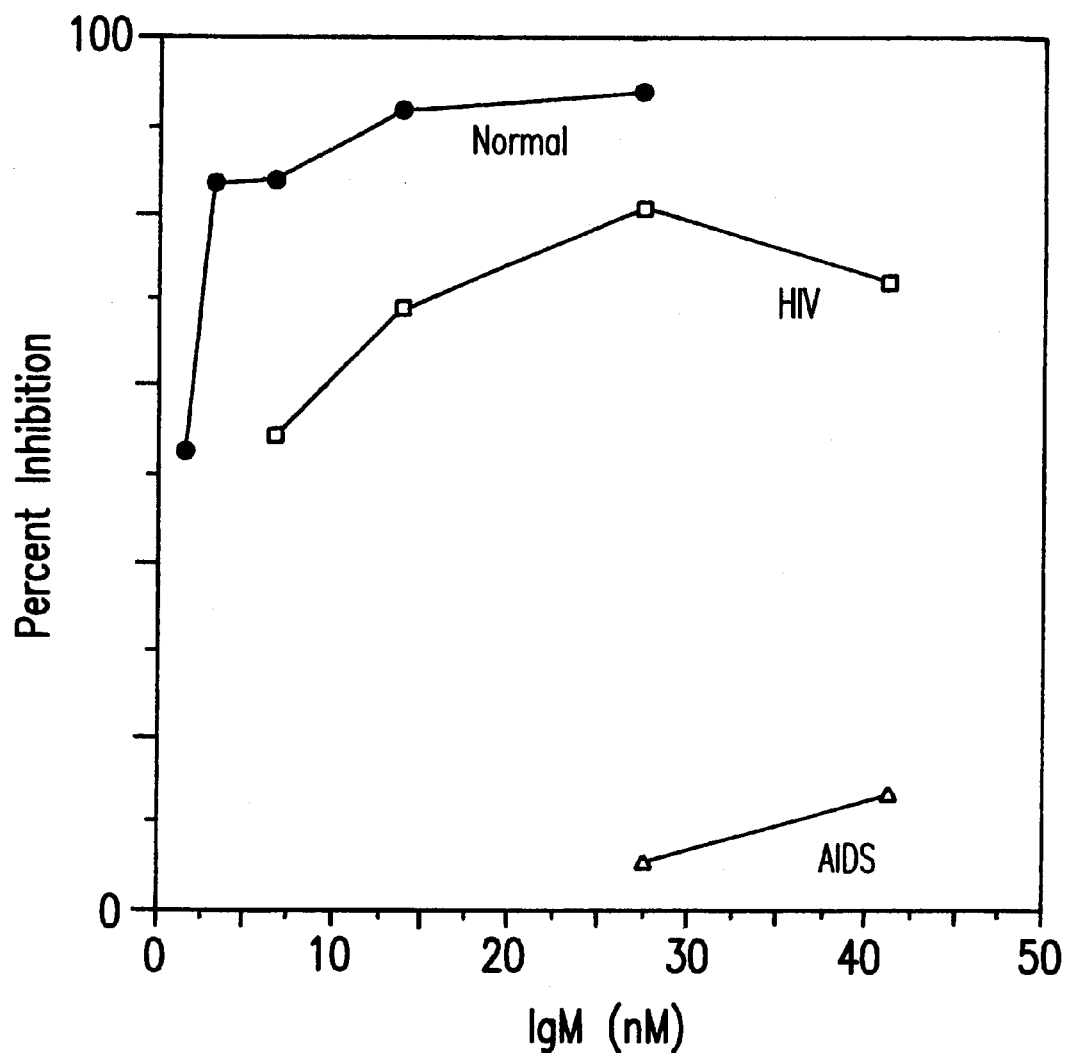
Figure 5B:
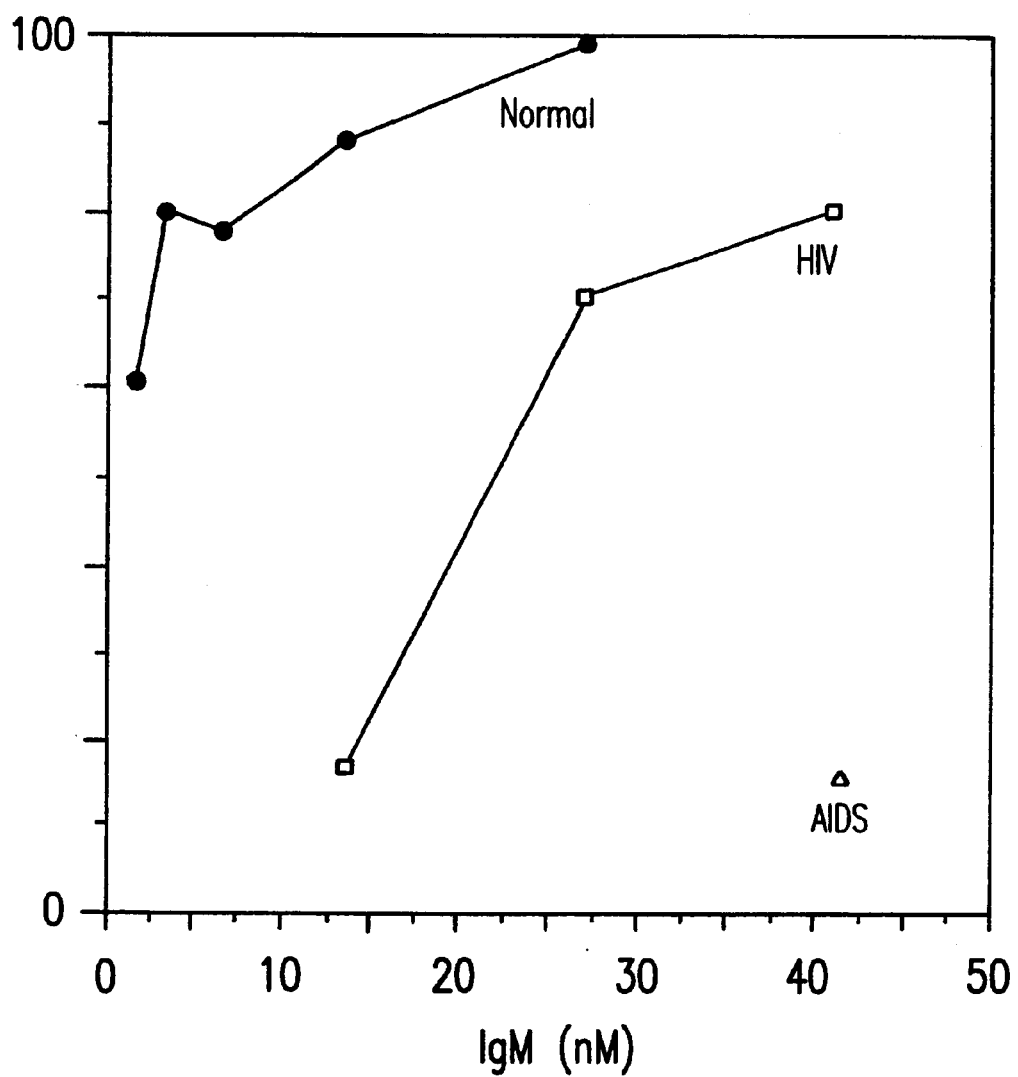

IgM anti-chemokine receptor autoantibodies contribute to the resistance against HIV-1 infection. FIGS. 5A–5C show the effect of various IgM antibodies on HIV-1 infectivity of Ghost cells. Referring first to FIG. 5A, which shows the percent inhibition by IgM of HIV-1 infectivity in Ghost CCR5 cells, it can be seen that Normal IgM and HIV IgM inhibit HIV-1 infectivity. No or minimal inhibitory effects are seen with AIDS IgM. Similar observations are seen when using IgM isolated from five individual normal sera and one HIV sera.

Interestingly, IgM from pooled normal sera partially inhibits (about 40 to 50% inhibition) HIV-1 infectivity with the R5 virus 8442 and the X4 virus RF, thereby suggesting that differences in epitope binding of virus and antibody may influence degree of inhibition.

The IgG antibody 2D7, a murine anti-CCR5 antibody, inhibited infectivity (by approximately 80%) of two of the three R5 viruses (i.e,. 8397 and 8442 but not 8658) when used at about 100 nM.

Similar inhibitory activity towards HIV-1 infectivity is obtained when using heat-inactivated (56° C.) normal human sera at final concentrations of about 8 to 15% (vol/vol) with culture media. Culture media containing about 15% pooled human serum is calculated to have about 168 nM IgM. HIV-1 infected sera and AIDS sera are not used, as the data would not be interpretable in the presence of anti-viral agents or IgG anti-HIV-1 antibodies. No inhibition of HIV-1 infectivity is detected with normal human IgG or albumin in this assay system. These data indicate that Normal IgM and HIV IgM when used in nM quantities inhibit HIV-1 infection of certain HIV-1 viral strains even though high doses of viruses are used, i.e., enough to infect about 8 to 20% cells with a single cycle of replication.

Several investigators have shown that normal human sera has no direct neutralizing activity towards the HIV-1 virus.

Others have shown that IgM anti-Tat and IgM anti-gp120 present in normal sera do not have HIV-1 neutralizing activity. This supports the concept that IgM-mediated inhibition of HIV-1 infectivity, such as observed herein, is mediated via reactivity of IgM to chemokine receptors and other lymphocyte-surface receptors important for HIV-1 entry into cells that are present on lymphocytes.

The results of the various studies, as discussed above, indicate that IgM purified from sera inhibits HIV-1 infectivity of cells. Purified IgM mediates inhibition of HIV-1 infectivity through binding of IgM to receptors important for HIV-1 entry into cells. Such receptors include, but are not limited to, CXCR4 and CCR5 receptors. IgM from normal sera has no direct anti-viral neutralizing effect and yet has the most inhibitory effect on HIV-1 infectivity. IgM purified from AIDS sera has minimal or no effect on HIV-1 infectivity, even though the AIDS IgM binds to Ghost cells and T cell lines and also enhances chemotaxis and cytosolic $Ca^{+2}$ induced by SDF-1. With respect to IgM binding and inhibition of HIV-1 infectivity, one plausible explanation for the observed difference between Normal IgM and HIV-1 IgM on the one hand and AIDS IgM on the other is that Normal IgM and AIDS IgM contain a heterogeneous group of IgM anti-lymphocyte antibodies with different binding epitopes that give rise to different functional effects.

The results suggest that the IgM antibody that inhibits SDF-1α binding on intact cells is probably the same IgM antibody that inhibits HIV-1 infectivity. AIDS IgM appears to lack this subset of IgM anti-lymphocyte antibody.

A second subset of IgM autoantibodies that binds to a different epitope enhances $Ca^{+2}$ flux in response to SDF-1α and enhances chemotaxis. This second subset of autoantibodies appears to be present in IgM from all sera (i.e., Normal, HIV-1 and AIDS) but is most prominent in AIDS IgM. This second subset of IgM anti-chemokine receptor antibody may be more important in influencing inflammatory states as it facilitates chemotaxis.

According to the present invention, IgM anti-lymphocyte autoantibodies limit the entry of the HIV-1 virus into cells and prolong the latency period because these antibodies bind to chemokine and other lymphocyte-surface receptors without lysing the cells at body temperature. The results shown herein indicate that disease progression to AIDS is associated with a marked reduction of IgM anti-lymphocyte autoantibodies, especially the subset of antibodies that inhibit HIV-1 entry into cells.

While not wishing to be bound to any particular theory, there are several possible explanations for the entry of the HIV-1 virus into cells and increased viral replication despite the presence of a good level of IgM autoantibody to chemokine receptor during the asymptomatic state. One such explanation is the possibility that there exists a delicate balance between these low-avidity binding IgM antibodies and the viral load. Factors that predispose an individual to an increased viral load or that inhibit the B cells secreting IgM autoantibodies will lead to viral entry into cells and to disease progression. It is also possible that the recently described subset of B cells expressing CD4, CXCR4 and CCR5 receptors may be the same subset that secretes IgM autoantibodies. Over the years, this B cell subset could be exhausted or could be infected with HIV-1, thereby leading to a decrease in antibody production. Additionally, one cannot underscore the importance of other host factors (e.g., anti-viral IgG antibodies, chemokines and complement and cytotoxic T cells) that decrease the viral load. Perturbation in any of these host defense mechanisms could lead to an increased viral load.

Secondly, it is possible that in some HIV-1 infected individuals, IgM anti-lymphocyte antibody may only partially prevent entry of certain HIV-1 viral isolates, as indicated by some of the studies herein. This latter mechanism may provide another explanation for disease progression despite the presence of IgM anti-chemokine receptor autoantibodies.

That IgM autoantibodies with specificity for CCR5 inhibit RANTES binding to CCR5 and inhibit macrophage-tropic HIV-1 virus from replicating supports the premise for a protective role mediated by these IgM anti-leukocyte antibodies. The use of human IgM anti-leukocyte antibodies to reduce HIV-1 infectivity (i.e., through receptor blockade) is an alternative approach for passive immunization, especially because it has been difficult to isolate human antibodies reactive to conserved neutralization epitopes on the HIV-1 virus. Receptor blockade employing IgM with reactivity to a broad range of chemokine and other receptors present on the lymphocytes may be particularly useful in situations where the HIV-1 virus switches its receptor usage, e.g., from CCR5 to CXCR4. Maintaining increased levels of such protective antibodies could also increase the latency period after HIV-1 infection.

The source of IgM antibodies may be heterologous, autologous or allogeneic. IgM antibodies with specificity for chemokine and other receptors on the leukocytes may be raised in vivo (i.e., in mice or other animals or in humans) or in vitro using cell culture techniques.

For example, IgM antibodies may be produced either in vivo or in vitro by genetic engineering whereby genes specific for IgM anti-lymphocyte antibodies are introduced into antibody-producing cells. These antibody-producing cells may then be introduced into an infected human or into immunodeficient animals where the cells produce IgM antibodies. In the alternative, these antibody-producing cells may be grown in vitro using hybridoma or other technology.

IgM antibodies with specificity for chemokine receptors may also be produced by isolating human antibody-producing cells specific for IgM antibodies and enhancing antibody production by such cells using hybridoma or other technology, including introduction of the cells into animals or humans. For example, human lymphocytes may be transplanted into immunodeficient mice, and the lymphocytes may then be stimulated with an agent that will activate B cells such as lipopolysaccharide ("LPS")

Another method of producing IgM antibodies is by isolating human antibody-producing cells capable of generating human IgM from animals such as, for example, the XenoMouse®. IgM antibody production by such cells may then be enhanced in vitro employing hybridoma or other technology such as, for example, stimulating the isolated lymphocytes with LPS or other agent that will activate the cells, e.g., the EBV virus.

IgM antibodies may also be produced in vitro by isolating, from an individual, lymphocytes that can be then transformed with the EBV virus and introduced in a culture. A subset of these EBV transformed B lymphocytes will secrete IgM antibodies such that the resulting culture fluid contains these antibodies.

In addition, viruses, bacteria and other antigens (e.g., mitogens) may be used to stimulate B cells in vivo to generate IgM antibodies to leukocytes.

IgM antibodies produced outside an infected individual may be delivered to the individual by one of several routes of administration including, but not limited to, intravenous and intramuscular delivery.

Having now fully described the invention with reference to certain representative embodiments and details, it will be apparent to one of ordinary skill in the art that changes and modifications can be made thereto without departing from the spirit or scope of the invention as set forth herein.

What is claimed is:

1. A method of inhibiting HIV cell entry comprising administering an effective amount of isolated heterogeneous anti-leukocyte receptor IgM antibody that targets at least one of the chemokine receptors selected from the group consisting of CCR5, CCR3, CXCR4, and CCR2B, and wherein said IgM antibody is effective to inhibit HIV cell entry.

2. The method of claim 1, wherein the chemokine receptors are present on autologous or allogenic lymphocytes of leukocytes.

3. The method of claim 1, wherein the IgM antibodies are administered to the individual intravenously or intramuscularly.

4. The method of claim 1 wherein the IgM antibodies are selected from the group consisting of human IgM antibodies and animal IgM antibodies.

5. The method of claim 4, wherein the human IgM antibodies are selected from the group consisting of Normal IgM antibodies, Waldenstrom IgM antibodies, or HIV IgM antibodies.

6. The method of claim 5, wherein the isolated B lymphocyte cells are stimulated in vitro by infection with the EBV virus.

7. The method of claim 1, wherein the IgM antibodies are produced by isolating human or animal antibody producing cells.

8. The method of claim 7, wherein the production of the IgM antibodies by the antibody-producing cells is enhanced using hybridoma technology or cell-culture techniques.

9. The method of claim 7 wherein the isolated human antibody producing cells are B-lymphocytes.

* * * * *